(12) United States Patent
Gunsel et al.

(10) Patent No.: US 7,195,828 B2
(45) Date of Patent: Mar. 27, 2007

(54) LUBRICANT FOR MAGNETIC RECORDING MEDIUM AND USE THEREOF

(75) Inventors: Selda Gunsel, The Woodlands, TX (US); Clifford Venier, The Woodlands, TX (US); I-Ching Chiu, Houston, TX (US)

(73) Assignee: Shell Oil Company, Houston, TX (US)

( * ) Notice: Subject to any disclaimer, the term of this patent is extended or adjusted under 35 U.S.C. 154(b) by 256 days.

(21) Appl. No.: 09/971,193

(22) Filed: Oct. 4, 2001

(65) Prior Publication Data

US 2002/0114980 A1 Aug. 22, 2002

Related U.S. Application Data

(63) Continuation-in-part of application No. 09/534,282, filed on Mar. 24, 2000.
(60) Provisional application No. 60/126,372, filed on Mar. 26, 1999.

(51) Int. Cl.
G11B 5/725 (2006.01)

(52) U.S. Cl. ............... 428/835.6; 428/841.2; 428/841.3; 508/221; 585/20; 585/23

(58) Field of Classification Search ......... 428/841.2, 428/841.3; 508/221; 585/20, 23
See application file for complete search history.

(56) References Cited

U.S. PATENT DOCUMENTS

| | | | | |
|---|---|---|---|---|
| 4,077,992 A | * | 3/1978 | Fusco | 554/223 |
| 4,163,729 A | * | 8/1979 | Adams | 508/156 |
| 4,566,983 A | | 1/1986 | Hayashi | |
| 4,693,799 A | | 9/1987 | Yanagihara | |

(Continued)

FOREIGN PATENT DOCUMENTS

| | | |
|---|---|---|
| EP | 0613886 A1 | 9/1994 |
| EP | 0613887 A1 | 9/1994 |
| FR | 2559606 A | 2/1984 |
| JP | 58222441 A | 12/1983 |
| JP | 10140169 | 5/1998 |
| JP | 2001-207183 | 7/2001 |
| WO | WO 98/07145 | 2/1998 |
| WO | WO 00/58956 A1 | 10/2000 |
| WO | WO 00/58956 | 10/2000 |

OTHER PUBLICATIONS

Lambert et al., The Triple Bond as a Potential Double Donor in Solvolytic Participation, *J. Org. Chem.*, 1975, pp. 633–636, vol. 40, No. 5.
Gream et al., The Camphenehydro (Methylcamphenilyl) and Isobornyl (Bornyl) Cations. Generation of the Enantiomeric Cations by the π and σ Routes of Solvolysis, *Aust. J. Chem.*, 1974, pp. 567–587, vol. 27, No. 3.
Partial search Report, Feb. 27, 2003.
A.J. Gellman, Lubricants and overcoats for magnetic storage media, Colloid & Interface Science, vol. 3, pp. 368–372, 1999.

(Continued)

*Primary Examiner*—Kevin M. Bernatz

(57) ABSTRACT

A magnetic recording medium and method for forming the magnetic recording medium are described. The magnetic recording medium includes a magnetic layer formed on a non-magnetic support, and a lubricant layer over the magnetic layer. The lubricant layer includes a compound selected from hydrocarbyl-substituted cyclopentanes, hydrocarbyl-substituted cyclopentenes, hydrocarbyl-substituted cyclopentadienes, and mixtures or derivatives thereof and, optionally, one or more additives. The lubricant layer also may be used on a magnetic head for reading and writing information on a magnetic recording medium. The magnetic recording medium and the magnetic head may be used to manufacture computer disk drives, compact disk drives, audio equipment, and video equipment.

11 Claims, 7 Drawing Sheets

U.S. PATENT DOCUMENTS

| | | | |
|---|---|---|---|
| 4,721,823 A | | 1/1988 | Venier et al. |
| 4,758,471 A | | 7/1988 | Arioka et al. |
| 4,849,566 A | | 7/1989 | Venier et al. |
| 4,863,622 A | * | 9/1989 | Chiu .......................... 508/444 |
| 4,929,782 A | | 5/1990 | Venier et al. |
| 5,012,022 A | | 4/1991 | Venier et al. |
| 5,012,023 A | | 4/1991 | Venier et al. |
| 5,026,577 A | | 6/1991 | Biresaw et al. |
| 5,084,516 A | | 1/1992 | Tsuchiya et al. |
| 5,128,216 A | | 7/1992 | Ng |
| 5,144,095 A | | 9/1992 | Venier et al. |
| 5,162,163 A | | 11/1992 | Ohta et al. |
| 5,310,439 A | | 5/1994 | Matsui et al. |
| 5,364,547 A | * | 11/1994 | Babb et al. ................. 508/569 |
| 5,525,392 A | | 6/1996 | Baum et al. |
| 5,541,351 A | | 7/1996 | Patsidis et al. |
| 5,578,237 A | | 11/1996 | Emert et al. |
| 5,578,741 A | | 11/1996 | Frey et al. |
| 5,677,051 A | | 10/1997 | Ueda et al. |
| 5,776,602 A | | 7/1998 | Ueda et al. |
| 5,821,027 A | | 10/1998 | Landry-Coltrain et al. |
| 5,874,169 A | | 2/1999 | Falcone |
| 6,103,677 A | | 8/2000 | Furutani et al. ............ 508/465 |
| 6,132,875 A | * | 10/2000 | Kiuchi et al. ................ 428/408 |
| 6,319,600 B1 | * | 11/2001 | Stirniman et al. .......... 428/336 |

OTHER PUBLICATIONS

C.M. Mare, Picking the best lube for contact recording, Data Storage, pp 45–49, Jul./Aug. 1997.

M. Yang et al., Cyclotriphosphazenes as Potential Lubricants for Thin Film Hard Disks, Tribology Transactions, vol. 28, No. 3, pp. 636–664, 1995.

S. Mori et al., Tribochemical Reactions at the Head–Disk Interface on Magnetic Recording Media, Proceedings of ASIA TRIB, pp. 300–303, Oct. 12–15, 1998.

Q. Zhao et al., Tribological Study of Phosphazene–Type Additives in Perfluoropolyether Lubricant for Hard Disk Applications, STLE Preprint, No 98–TC–4C–1, pp. 1–6, 1998.

F.E. Talke, On tribological problems in magnetic disk recording technology, Wear, vol. 190, pp. 232–238, 1995.

C.G. Venier et al., Tris(2–Octyldodecyl)Cyclopetane, a Low Volatility, Wide Liquid–Range, Hydrocarbon Fluid, Unknown Publication, pp. 13.1–1–13.1–12.

E.W. Casserly et al., Tribologically Relevant Properties of Multyply–Alkylated Cyclopentanes. The Design of a Hydrocarbon Molecule for Aerospace Applications, Symposium on Chem. Lub. and Lubrication, American Chem Society, Boston, vol. 35, No. 2, pp. 265–271, Apr. 22–27, 1990.

G.G. Venier et al., Multiply–Alkylated Cyclopentanes (MACs): A New Class of Synthesized Hydrocarbon Fluids, Lubrication Engineering, vol. 47, No. 7, pp. 586–591, 1991.

G.G. Venier et al., Preparation of a New Class of Synthetic Lubricants, Multiply–Alkylated Cyclopentanes (MACs), Symposium on Chem. Lub. and Lubicants, American Chem. Society, Boston, vol. 35, No. 2, pp. 260–264, Apr. 22–27, 1990.

Vasil'EV et al., Compounds with an Herbal Odor VI.* The E Isomers of the Structural Analogs of Leaf Alcohol, Russian J. of Org. Chem., vol. 30, No. 6, pp. 870–875, 1994.

AL–Qallaf et al., Metal (IV) phosphate catalysed retro–Prins reaction involving an oxetane intermediate, J. Chem. Soc., Perlan Trans. 2, pp. 1421–1423, 1999.

Bartlett et al., Nucleophilic Reactivity of the Carbon–Carbon Double Bond. II. Solvolytic Ring Closure of 2–(3–Methyl– and 3,4 dimethyl –$\Delta^3$–cyclopentenyl)ethyl ρ–Nitrobenzenesulfonates, J. of Am. Chem. Soc., vol. 87, No. 6, pp. 1297–1307, 1965.

Vasil'Ev et al., Compounds with a Herbal Odor II.* CIS–1–(2–Hydroxyethyl)–2–Ethylcycloalkanes and Their Analogs, J. of Org. Chem. ofU.S.S.R., vol. 27, No. 2, pp. 273–278, 1991.

Suzuki et al., Vinylic Organoboranes. 1. A.Convenient Sythesis of Acetylenes via the Reaction of Lithium (1–Alkynyl) organoborates with Iodine, J. Org. Chem., vol. 51, No. 24, pp. 4507–4511, 1986.

Aldridge et al., Metabolites of Lasiodiplodia theobromae, J. Chem. Soc, Sect. C: Organic Chem., pp. 1623–1627, 1971.

Boatto et al., Amides and Formamidines with Antinociceptive Activity, Farmaco, vol. 48, No. 9, pp. 1279–1289, 1993.

Aldrich Catalogue Nederland, Cyclopentene, pp. 377, 1992.

Merck Index $11^{th}$ Ed., Cyclopentadiene and Cyclopentane, pp. 2741, 1989.

Shawe et al., Iterative Reductive Alkylation Approach to Alkaloids: A Synthesis of(±)–Monomorine Land Its C–3 Epimer, J. Org. Chem., vol. 59, pp. 5841–5842, 1994.

Hutchins et al., Stereoselective Reductions of Substituted Cyclohexyl and Cyclopentyl Carbon–Nitrogen π Systems with Hydride Reagents, J. Org. Chem., vol. 48, No. 20, pp. 3412–3422, 1983.

Ayerst et al., cis– and trans–3: 4–cyclo Pentanopiperidine, J. Org. Chem. Soc., pp. 4097–4104, 1958.

Masse et al., Lewis Acid–Mediated Carbocyclization Reactions of Chiral (E)–Crotylsilanes, J. Org. Chem., vol. 62, No. 26, pp. 9335–9338, 1997.

Fraenkel et al., Structure and Dynamic Behavior of Crowded Cis Vicinal [(N,N–Dimethylamino)cyclopentyl] trimethylammonium Salts and Related Compounds, J. Am. Chem. Soc., vol. 118, No. 50, pp. 12804–12811, 1996.

Snowden et al., Dienamines as Diels–Alder Dienes. An Efficient Cyclohexannulation Sequence, Tetrahedrom Letters, vol. 27 No. 6, pp. 699–702, 1986.

Suemune et al., Conversion of Limonene to Prostanoic Acid and 8–Isoprostanic Acid, Chem. Pharm. Bull., vol. 34, No. 2, pp. 550–557, 1986.

Gustavsson et al., Enantiomers of Cis– and Trans–3–(4–propyl–cyclopent–2–enyl) Propyl Acetate. A Study on the Bioactive Conformation and Chiral Recognition of a Moth Sex Pheromone Component, Bioorg. Med. Chem., vol. 5, No. 12, pp. 2173–2183, 1997.

Fujisawa et al., The Regiospecific Synthesis of Vicinally Dialkylated Cyclopentadienes and Its Application to a Sysnthesis of Allethrolone, Chem. Letters., No. 9, pp. 943–946, 1976.

Kramp et al., Synthesis of Enantiomerically Pure ent–Multifidene and Related Compounds, J. Chem. Soc. Chem. Conn., No. 6, pp. 551–552, 1993.

Search Report, Sep. 8, 2000.

Derwent Translation of FR 2559606 (Derwent Acc. No. 1985–238531).

Encylclopedia of Chemical Technology, $4^{th}$ Ed., vol. 15, pp. 485–486 (1995).

G.E.Gream, et al., The Camphenehydro (Methylcamphenilyl) and Isobornyl (Bornyl) Cations. I. Generation of the Enantiomeric cations by the pi and sigma routes of solvolysis, Aust. J. of Chem., vol. 27, No. 3, 1974, pp. 567–587.

J.B. Lambert et al., The Triple Bond as a Potential Double Donor in Solvolytic Participation, Journal of Organic Chem., vol. 40, No. 5, Mar. 1975, pp. 633–636.

* cited by examiner

LUBRICANT FOR MAGNETIC RECORDING MEDIUM AND USE THEREOF

CROSS REFERENCE TO RELATED APPLICATIONS

This patent application is a continuation-in-part of U.S. application Ser. No. 09/534,282, filed Mar. 24, 2000, entitled "Lubricant for Magnetic Recording Medium and Use Thereof," in the names of Selda Gunsel, Clifford Venier, and I-Ching Chiu which claims priority to U.S. Provisional Application Ser. No. 60/126,372, entitled "Lubricant for Magnetic Recording Medium and Use Thereof," filed on Mar. 26, 1999.

The disclosures of the aforementioned applications are incorporated by reference in their entirety herein.

FIELD OF THE INVENTION

The invention relates to a method of manufacturing a magnetic recording medium having a lubricant film formed thereon. Furthermore, the invention also relates to a data recording/retrieval device which incorporates such magnetic recording media.

BACKGROUND OF THE INVENTION

Thin-film magnetic recording disks and disk drives are commonly used for storing a large amount of data in magnetizable form. Over the last decade, magnetic recording has become the predominant technology for the storage of digital information in modern computer systems.

Magnetic recording generally is accomplished by the relative motion between a magnetic medium and a magnetic recording head. A magnetic recording head consists of a small electromagnet with a gap facing the magnetic medium. During writing, a current is applied to the windings of the electromagnet, thus creating a fringing field at the head gap and magnetizing the magnetic medium according to the direction of the current applied to the head. During reading, the flux from the magnetic medium is intercepted from the head core, inducing a voltage pulse in the coil of the read head.

FIGS. 1A and 1B illustrate a typical disk drive. FIG. 1A is a top plan view of the disk drive, and FIG. 1B is a side view of the disk drive. The disk drive 10 generally includes a magnetic disk 11 and a disk head 16 for writing and reading information to and from the magnetic disk 11. The disk head 16 may include a read/write element 12 and a slider 13. The disk head 16 is connected to a suspension arm 14, which is, in turn, connected to a rotary actuator 15.

Two widely used methods to store and retrieve data are commonly referred to as contact start/stop (CSS) and ramp load/unload. In each design, rotation of the magnetic disk produces an air layer between the head and the surface of the disk. In this state, recording or reproduction of data is performed. Occasionally, however, a slight change in altitude of the head renders the load on the head non-uniform, causing contact to occur. Such contact may result in damage to the head and the surface of the magnetic disk for both CSS and ramp/load unload designs.

At the end of the operation, the rotation of the magnetic disk is stopped. In contact start/stop (CSS) designs, the head is allowed to rest on a laser textured landing zone on the surface at the edge of the magnetic disk. In ramp load/unload designs, the sliding head is completely removed from the disk prior to the air bearing collapsing. However, occasional impact between the sliding head and the magnetic disk still occurs, particularly during start-up (loading) conditions before the air film has stabilized.

To prevent the wear of the magnetic disk caused by the contact with and sliding on the head, a lubricant layer is provided on the surface of the magnetic disk. A common lubricant used in magnetic disks is perfluoropolyether ("PFPE"). To increase the wear resistance of the magnetic disk and to protect the magnetic material from the corrosive effect of the PFPE lubricant, a protective layer is sometimes provided between the magnetic medium and the lubricant layer. The protective layer may include amorphous carbon, diamond-like carbon, and other materials.

Due to the prevalent use of computers, increases in the areal data storage density of a magnetic disk have continued rapidly and unabatedly for almost 40 years. The trend towards high recording densities is expected to continue. For example, the current areal density is about 10 gigabytes per square inch. The next generation disks are going to have an areal density of about 50 gigabytes per square inch. In a few years, the areal density is expected to exceed 40 gigabytes per square inch. To achieve a high recording density, the magnetic head should be positioned as close as possible to the surface of the magnetic medium. The distance between the tip of the magnetic head and the surface of the magnetic medium is referred to as "flight height." For example, to achieve an areal density of about 10 gigabytes per square inch, a flight height in the range of about 10–15 nm is required. If an areal density of 40 gigabytes per square inch is desired, the flight height should be further decreased to about 3.5 nm. This means that the thickness of the lubricant layer (or film) and the thickness of the protective layer should sum to about 3 nm or less. Consequently, the reliability of the head-disk interface becomes more dependent on the life and performance of the lubricant film as the conquest for higher density disks continues. In other words, the characteristics of the lubricant film, such as its physical, chemical, and tribological properties, have a critical impact on the performance of such high density disks.

First, the lubricant film or layer should last for the lifetime of the drive. If the lubricant layer wears away prematurely, the disk drive would fail accordingly. Furthermore, the lubricant layer should be resistant to chemical degradation. Chemical degradation of the lubricant layer can be induced by thermal decomposition, catalytic reaction with solid surfaces, and mechanical shearing due to high-speed contact with the disk head.

In addition to chemical stability, a major challenge in developing disk lubricant systems is to provide adequate durability without increasing stiction to unacceptable levels. During the lifetime of a magnetic disk, the disk head goes through thousands of stop-and-start cycles. If the static friction forces between the disk head and the magnetic medium become too large, the drive motor may not develop sufficient torque to restart disk spinning. This may lead to failure of the disk drive.

As mentioned above, PFPEs have been used extensively to form a lubricant film in a magnetic recording medium. PFPEs are relatively expensive. Therefore, cheaper alternatives are more desirable. Although PFPEs have good thermal stability, they decompose readily when they are in contact with Lewis acids. This is an important consideration because the head often is fabricated from an $Al_2O_3$/TiC composite, and $Al_2O_3$ can be converted to $AlF_3$, a strong Lewis acid. This formation of $AlF_3$ leads to chemical degradation of PFPE lubricants. Moreover, use of chlorofluorohydrocarbons ("CFCs") as solvents generally is involved when PFPEs are applied to a magnetic medium as PFPEs are not compatible with many other hydrocarbon based solvents. CFCs have detrimental effects on the ozone layer, and use thereof should be avoided, if possible.

In view of the foregoing discussion, in order to meet the challenge of the information age, there is a need to develop magnetic recording media with a lubricant layer that is more chemically and mechanically robust to withstand high shear rates and harsh environments. The lubricant layer should allow decreased flight height so that higher areal densities may be achieved. Furthermore, it is desirable that such lubricant be relatively inexpensive, environmentally friendly, that no CFCs be used in forming the lubricant layer, and that the materials used in the lubricant layer be compatible with a range of hydrocarbon solvents.

SUMMARY OF THE INVENTION

The above need is met by a class of hydrocarbyl-substituted cyclopentenes, hydrocarbyl-substituted cyclopentanes, hydrocarbyl-substituted cyclopentadienes, and mixtures or derivatives thereof which may be used to form a lubricant layer over a magnetic layer in a magnetic recording medium.

In one aspect, the invention relates to a magnetic recording medium. The magnetic recording medium includes: (1) a non-magnetic substrate; (2) a magnetic layer formed on the substrate; (3) a lubricant layer over the magnetic layer, where the lubricant layer includes a compound selected from the group consisting of hydrocarbyl-substituted cyclopentanes, hydrocarbyl-substituted cyclopentenes, hydrocarbyl-substituted cyclopentadienes, and mixtures or derivatives thereof. In some embodiments, the hydrocarbyl-substituted cyclopentanes, hydrocarbyl-substituted cyclopentenes, hydrocarbyl-substituted cyclopentadienes, and mixtures or derivatives thereof are optionally combined with one or more additives. In some embodiments, the magnetic recording medium may further include a protective layer, such as a carbon overcoat, between the magnetic layer and the lubricant layer. In other embodiments, the hydrocarbyl substituent on the cyclopentane, cyclopentene, and cyclopentadiene may include one or more functional groups, such as hydroxy, carboxylic acid, amine, carboxylic ester, carboxylic amide, phosphate, or sulfur-containing compounds, etc.

In another aspect, the invention relates to a magnetic head. The head includes: (1) a head body; and (2) a lubricant layer over at least a portion of the head body, where the lubricant layer includes a compound selected from the group consisting of hydrocarbyl-substituted cyclopentanes, hydrocarbyl-substituted cyclopentenes, hydrocarbyl-substituted cyclopentadienes, and mixtures or derivatives thereof. In some embodiments, the hydrocarbyl-substituted cyclopentanes, hydrocarbyl-substituted cyclopentenes, hydrocarbyl-substituted cyclopentadienes, and mixtures or derivatives thereof are optionally combined with one or more additives. In some embodiments, the hydrocarbyl substituent on the cyclopentane, cyclopentene, and cyclopentadiene may include one or more functional groups, such as hydroxy, carboxylic acid, amine, carboxylic ester, carboxylic amide, phosphate, or sulfur-containing compounds, etc.

Additional aspects of the invention are described herein. Advantages and objects of the invention are apparent from the following description.

DETAILED DESCRIPTION OF EMBODIMENTS OF THE INVENTION

Figure 1A:
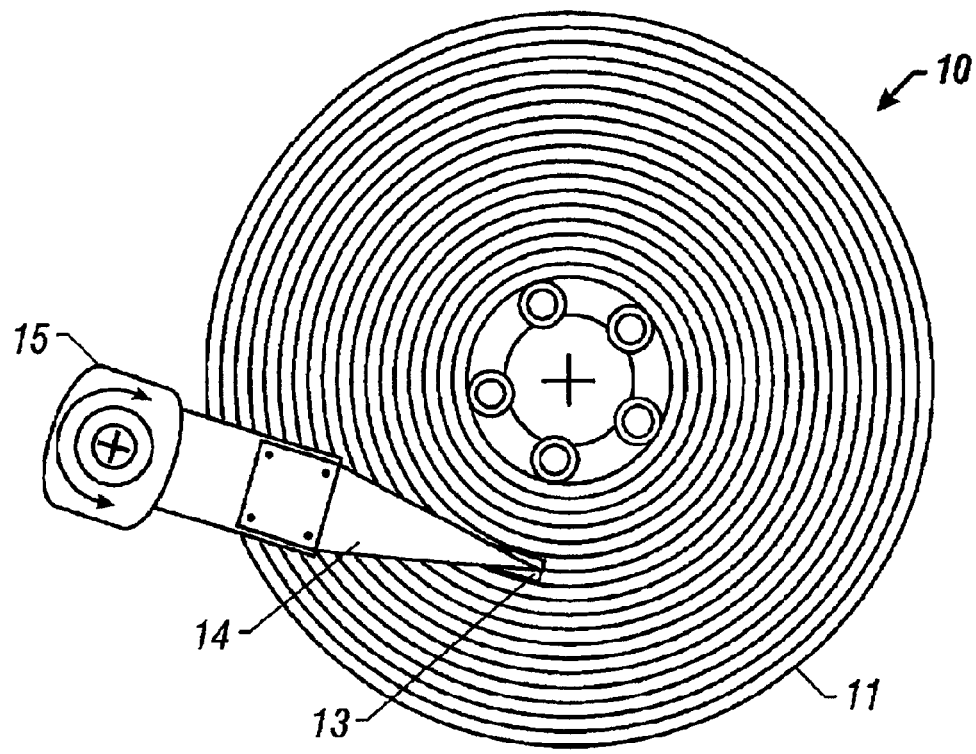
FIG. 1A is a schematic showing the top plan view of a typical computer disk drive system.
Figure 1B:
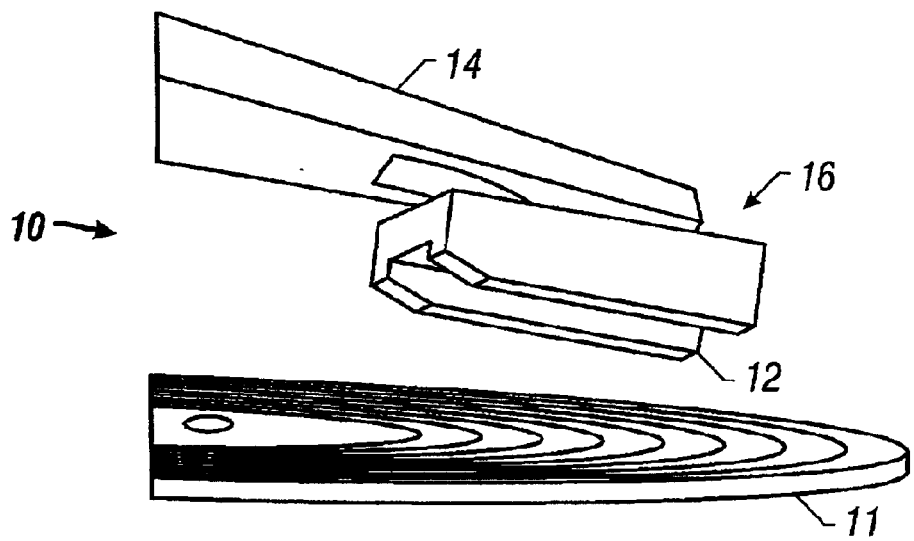
FIG. 1B is a schematic showing a side view of the computer disk drive system of FIG. 1A.

Embodiments of the invention provide a magnetic recording medium with a lubricant film or layer formed from a class of hydrocarbyl-substituted cyclopentadienes, hydrocarbyl-substituted cyclopentenes, hydrocarbyl-substituted cyclopentanes, and mixtures or derivatives thereof. This class of compounds also may be used as a lubricant layer on a magnetic head for reading and writing on a magnetic recording medium. The magnetic recording medium, the magnetic head, or both are useful in manufacturing data recording/retrieval devices, such as a computer disk drive.

Although "hydrocarbyl" is generally understood to mean an organic group that includes only carbon and hydrogen, the term is used herein to refer to both functionalized hydrocarbyl and non-functionalized hydrocarbyl. Functionalized hydrocarbyl refers to an organic group that includes carbon, hydrogen, and a functional group (e.g., a polar group), whereas non-functionalized hydrocarbyl refers to an organic group that includes only carbon and hydrogen. A derivative of a hydrocarbyl-substituted cyclopentane refers herein to any compound that is derived from the hydrocarbyl-substituted cyclopentane. Derivation may occur on the hydrocarbyl or the cyclopentane group. Preferably, derivation should occur on one or more of the hydrocarbyl groups by introducing one or more polar groups. The derivation may be achieved either before or after the hydrocarbyl-substituted cyclopentane is prepared. A derivative of hydrocarbyl-substituted cyclopentadienes and hydrocarbyl-substituted cyclopentenes is similarly defined herein.

Since a lubricating film on a magnetic recording medium is exposed to atmospheric conditions and is applied only once during the manufacturing process, the lubricant in the form of a film over a magnetic recording medium preferably should have low vapor pressure, high chemical stability, good load-carrying capability, and desirable tribological properties. Substituted cyclopentanes, cyclopentenes, and cyclopentadienes possess the requisite properties for use as a lubricant film or layer in a magnetic recording medium. Some embodiments utilize oligomeric cyclopentane, cyclopentene, and cyclopentadiene derivatives prepared by reacting cyclopentadienes or alkyl-substituted cyclopentadienes with polyhydric alcohols followed by hydrogenation, if appropriate.

Lubricants

As mentioned above, suitable compounds for forming a lubricant layer or film over a layer of magnetic material include hydrocarbyl-substituted cyclopentanes, hydrocarbyl-substituted cyclopentenes, hydrocarbyl-substituted cyclopentadienes, and mixtures or derivatives thereof. These compounds are selected because they have low vapor pressure and desired tribological properties. These compounds are also selected because they prevent adhesion, assist in controlling the friction level, and assist in preventing deep asperity penetration. For example, tris-(2-octyldodecyl) cyclopentane has a vapor pressure of about $1 \times 10^{-12}$ Torr at about 20° C. Its tribological properties are better or comparable to some of the existing lubricants for magnetic recording media. In addition, it has good thermal stability, additive solubility, and oxidation resistance.

Suitable hydrocarbyl-substituted cyclopentanes generally have the following formula:

where $R^1$ and $R_2$ are hydrocarbyl groups, respectively, m and n are zero or positive integers, respectively. Preferably, the sum of m and n should be less than 6, although compounds with m+n exceeding six are also suitable in embodiments of the invention. It should be understood that either or both $R_1$ and $R_2$ may be further derivatized to include any polar groups.

Suitable hydrocarbyl-substituted cyclopentenes generally have the following formula:

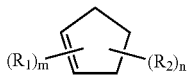

where $R_1$ and $R_2$ are hydrocarbyl groups, respectively, m and n are zero or positive integers, respectively. Preferably, the sum of m and n should be less than 6, although compounds with m+n exceeding six are also suitable in embodiments of the invention. It should be understood that the double bond can be located anywhere in the ring. Furthermore, either or both $R_1$ and $R_2$ may be further derivatized to include any polar groups.

Suitable hydrocarbyl-substituted cyclopentenes generally have the following formula:

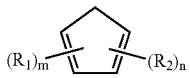

where $R_1$ and $R_2$ are hydrocarbyl groups, respectively, m and n are zero or positive integers, respectively. Preferably, the sum of m and n should be less than 6. Either or both $R_1$ and R2 may be further derivatized to include any polar groups.

It should be understood that any one of the compounds represented by the above formulas may be used alone or in combination with another compound or an additive. Methods for synthesizing these compounds have been disclosed in the following patents: (1) U.S. Pat. No. 4,721,823; (2) U.S. Pat. No. 4,849,566; (3) U.S. Pat. No. 4,929,782; (4) U.S. Pat. No. 5,012,022; (5) U.S. Pat. No. 5,012,023; and (6) U.S. Pat. No. 5,144,095. The disclosures of all of the above patents are incorporated by reference in their entirety herein.

In preferred embodiments, $R_1$ is an alkyl group of one to about thirty-six carbon atoms. $R_2$ is also a hydrocarbyl group containing from one to about thirty-six carbon atoms. $R_1$ and $R_2$ may the same or different hydrocarbyl groups. Preferably, they are a straight or branched alkyl group of four to 36 carbon atoms. For example, $R_1$ and $R_2$ maybe selected from the following hydrocarbyl groups: methyl, ethyl, propyl, n-butyl, n-hexyl, n-octyl, n-decyl, n-dodecyl, n-tetradecyl, iso-dodecyl, iso-tridecyl, 2-ethyl-1-hexyl, 2-octyl-1-dodecyl, 2-decyl-1-tetradecyl, 2-octyl, and t-butyl. It should be noted that the term "hydrocarbyl" used herein includes, but is not limited to, the above examples.

Preferably, m is 0, 1, 2, or 3, although it may be any other positive integer. Preferably, n is an integer ranging from two to six, although it may be 0 or any other positive integer. Preferably, the sum of m and n should not be greater than six, although compounds with m+n exceeding six are also suitable in embodiments of the invention.

The following is a list of preferred cyclopentanes, cyclopentenes, and cyclopentadienes suitable for use as a lubricant in magnetic recording media. It should be understood that the following compounds are merely exemplary and are not intended to limit the scope of the invention as otherwise described herein.

Non-limiting examples of suitable cyclopentanes include: Tri-n-octyl cyclopentane; Tetra-n-octyl cyclopentane; Penta-n-octyl cyclopentane; Tri-n-nonyl cyclopentane; Tetra-n-nonyl cyclopentane; Penta-n-nonyl cyclopentane; Tri-n-decyl cyclopentane; Tetra-n-decyl cyclopentane; Penta-n-decyl cyclopentane; Tri-n-undecyl cyclopentane; Tetra-n-undecyl cyclopentane; Penta-n-undecyl cyclopentane; Tri-n-dodecyl cyclopentane; Tetra-n-dodecyl cyclopentane; Penta-n-dodecyl cyclopentane; Tri-2-ethylhexyl cyclopentane; Tetra-2-ethylhexyl cyclopentane; Di-n-oxtyl, n-decyl cyclopentane; n-octyl, di-n-decyl cyclopentane; Trioctyl, n-decyl clopentane; Di-n-octyl, di-n-decyl cyclopentane; n-octyl, tri-n-decyl cyclopentane; Tri-n-tridecyl cyclopentane; Tetra-n-tridecyl cyclopentane; Penta-n-tridecyl cyclopentane; Di-(2-octyl-1-dodecyl)cyclopentane; Tris-(2-octyl-1-dodecyl)cyclopentane; and Tetra-(2-octyl-1-dodecyl) cyclopentane.

Non-limiting examples of suitable cyclopentenes include: Tri-n-octyl cyclopentene; Tetra-n-octyl cyclopentene; Penta-n-octyl cyclopentene; Tri-n-nonyl cyclopentene; Tetra-n-nonyl cyclopentene; Penta-n-nonyl cyclopentene; Tri-n-decyl cyclopentene; Tetra-n-decyl cyclopentene; Penta-n-decyl cyclopentene; Tri-n-undecyl cyclopentene; Tetra-n-undecyl cyclopentene; Penta-n-undecyl cyclopentene; Tri-n-dodecyl cyclopentene; Tetra-n-dodecyl cyclopentene; Penta-n-dodecyl cyclopentene; Tri-2-ethylhexyl cyclopentene; Tetra-2-ethylhexyl cyclopentene; Di-n-octyl, n-decyl cyclopentene; n-octyl, di-n-decyl cyclopentene; Trioctyl, n-decyl cyclopentene; Di-n-octyl, di-n-decyl cyclopentene; n-octyl, tri-n-decyl cyclopentene; Tri-n-tridecyl cyclopentene; Tetra-n-tridecyl cyclopentene; Penta-n-tridecyl cyclopentene; Di-(2-octyl-1-dodecyl)cyclopentene; Tris(2-octyl-1-dodecyl)cyclopentene; and Tetra-(2-octyl-1-dodecyl) cyclopentene.

Non-limiting examples of suitable cyclopentadienes include: Tri-dodecyl cyclopentadiene; Tetra-dodecyl cyclopentadiene; Penta-dodecyl cyclopentadiene; Penta-n-butyl cyclopentadiene; Penta-n-octyl cyclopentadiene; Penta-n-nonyl cyclopentadiene; Penta-n-decyl cyclopentadiene; Di-n-octyl, n-decyl cyclopentadiene; n-octyl, di-n-decyl cyclopentadiene; Trioctyl, n-decyl cyclopentadiene; Di-n-octyl, di-n-decyl cyclopentadiene; n-octyl, tri-n-decyl cyclopentadiene; Tri-n-tridecyl cyclopentadiene; Tetra-n-tridecyl cyclopentadiene; Penta-n-tridecyl cyclopentadiene; Di-(2-octyl-1-dodecyl)cyclopentadiene; Tris-(2-octyl-1-dodecyl) cyclopentadiene; Tetra-(2-octyl-1-dodecyl)cyclopentadiene; Di-n-octyl-Tri-n-decyl cyclopentadiene; Tri-n-octyl-Di-n-decyl cyclopentadiene; Methyl-n-octyl-n-decyl cyclopentadiene; Methyl-Di-n-octyl-n-decyl cyclopentadiene; Methyl-Tri-n-octyl-n-decyl cyclopentadiene; Methyl-n-octyl-di-n-decyl cyclopentadiene; Methyl-n-octyl-tri-n-decyl cyclopentadiene; Dimethyl-n-octyl-n-decyl cyclopentadiene; Dimethyl-di-n-octyl-n-decyl cyclopentadiene; Dimethyl-n-octyl-di-n-decyl cyclopentadiene; n-nonyl-n-decyl-n-undecyl cyclopentadiene; Di-n-nonyl-n-decyl-n-undecyl cyclopentadiene; n-nonyl-di-n-decyl-n-undecyl cyclopentadiene; and n-nonyl-n-decyl-di-n-undecyl cyclopentadiene.

Derivatized cyclopentanes, cyclopentenes, and cyclopentadienes maybe represented by the following formulas:

1. Derivatized Cyclopentanes

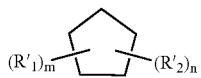

2. Derivatized Cyclopentenes

3. Derivatized Cyclopentadienes

wherein $R'_1$ and $R'_2$ are hydrocarbyl groups which may or may not be derivatized respectively; m and n are zero or positive integers (such as 1, 2, 3, 4, 5, . . . ), respectively. Preferably, the sum of m and n should be less than 6. When $R'_1$ or $R'_2$ is a derivatized hydrocarbyl group, it may include, but not limited to, the following functional groups: —OH; —NH$_2$; carboxylic acid; carboxylic ester; phenolic ester; polyether; amide; amine; sulfonamide; thiophosphate; and phosphate.

For example, a cyclopentane, cyclopentene, or cyclopentadiene which includes a polyether or a hydroxyl group may be represented by the following formulas:

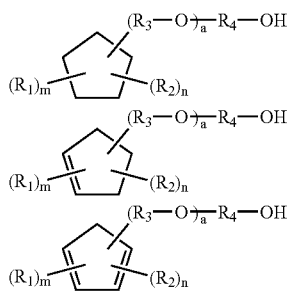

wherein a is any integer, such as 0, 1, 2, 3, 4, 5, 6, 7, 8, 9, or 10; m and n can be zero or any positive integers. Preferably, the sum of m and n should be less than 5, although compounds with m+n exceeding five are also suitable in embodiments of the invention. $R_1$, $R_2$, $R_3$, and $R_4$ are individually a hydrocarbyl group, which may or may not include a polar group.

A cyclopentane, cyclopentene, or cyclopentadiene which includes a phosphate or thiophosphate group may be represented by the following formulas:

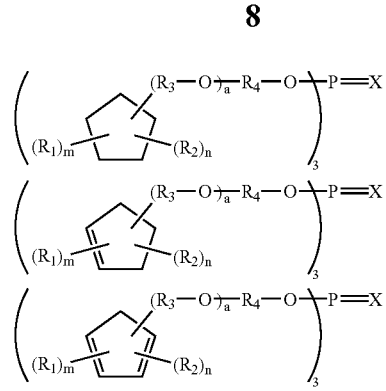

wherein a is any integer, such as 0, 1, 2, 3, 4, 5, 6, 7, 8, 9, or 10; m and n can be zero or any positive integers. Preferably, the sum of m and n should be less than 5, although compounds with m+n exceeding five are also suitable in embodiments of the invention. $R_1$, $R_2$, $R_3$, and $R_4$ are individually a hydrocarbyl group, which may or may not include a polar group; X is either oxygen or sulfur.

A cyclopentane, cyclopentene, or cyclopentadiene which includes a carboxylic acid, carboxylic ester, phenolic ester, or amide group may be represented by the following formulas:

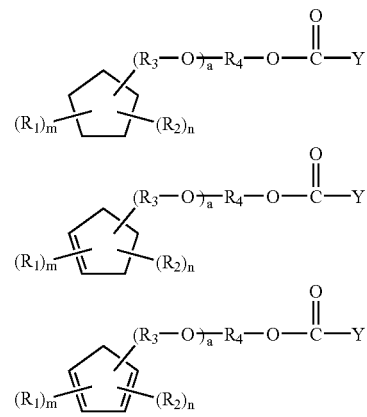

wherein a is any integer, such as 0, 1, 2, 3, 4, 5, 6, 7, 8, 9, or 10; m and n can be zero or any positive integers. Preferably, the sum of m and n should be less than 5, although compounds with m+n exceeding five are also suitable in embodiments of the invention. $R_1$, $R_2$, $R_3$, and $R_4$ are individually a hydrocarbyl group, which may or may not include a polar group; Y may be

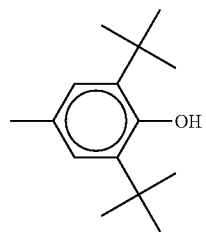

—OH; —NH$_2$; and $C_bF_{2b+1}$ (in which b is 1, 2, 3, . . . , or 40) where $C_bF_{2b+1}$ is straight or branched.

A suitable example of a cyclopentane which includes a carboxylic ester which may be used as a lubricant in magnetic recording media may be represented by the following formula:

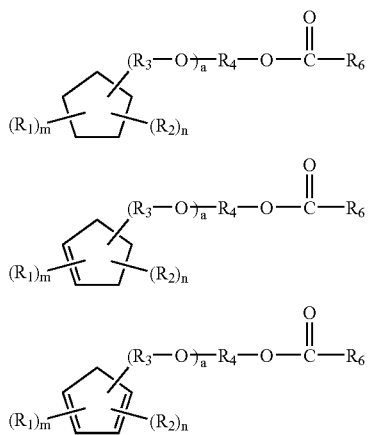

wherein a is any integer, such as 0, 1, 2, 3, 4, 5, 6, 7, 8, 9, or 10; m and n can be zero or any positive integers. Preferably, the sum of m and n should be less than 5, although compounds with m+n exceeding five are also suitable in embodiments of the invention. $R_1$, $R_2$, $R_3$, and $R_4$ are individually a hydrocarbyl group, which may or may not include a polar group. $R_6$ is a $C_pF_{2p+1}$, where $C_pF_{2p+1}$ is straight or branched and p can be one or any positive integers. Preferably, p is less than 40 although compounds with p exceeding 40 are also suitable in embodiments of the invention. In some embodiments, p is an integer from 1 to 20.

A cyclopentane, cyclopentene, or cyclopentadiene which includes an amine group may be represented by the following formulas:

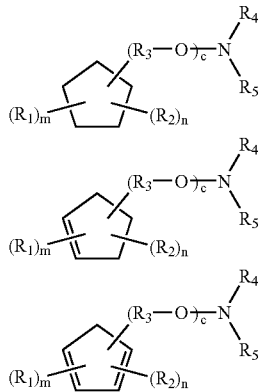

wherein c is any integer, such as 0, 1, 2, 3, 4, 5, 6, 7, 8, 9, or 10; m and n can be zero or any positive integers. Preferably, the sum of m and n should be less than 5, although compounds with m+n exceeding five are also suitable in embodiments of the invention. $R_1$, $R_2$, $R_3$, $R_4$, and $R_5$ are individually a hydrocarbyl group, which may or may not include a polar group; $R_4$ and $R_5$ may also be hydrogen individually.

A cyclopentane, cyclopentene, or cyclopentadiene which includes a sulfonamide group may be represented by the following formulas:

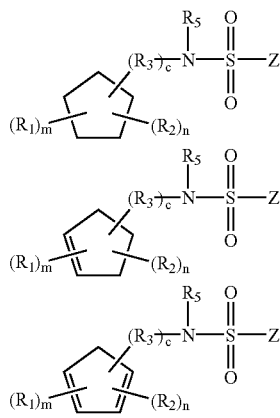

wherein c is any integer, such as 0, 1, 2, 3, 4, 5, 6, 7, 8, 9, or 10; m and n can be zero or any positive integers. Preferably, the sum of m and n should be less than 5, although compounds with m+n exceeding five are also suitable in embodiments of the invention. $R_1$, $R_2$, $R_3$, and $R_5$ are individually a hydrocarbyl group, which may or may not include a polar group; $R_5$ may also be hydrogen; Z may be a hydrocarbyl group or $C_bF_{2b+1}$ (in which b is 1, 2, 3, . . . , or 40) where $C_bF_{2b+1}$ is straight or branched.

A cyclopentane, cyclopentene, or cyclopentadiene which includes a dimeric amine linkage may be represented by the following formulas:

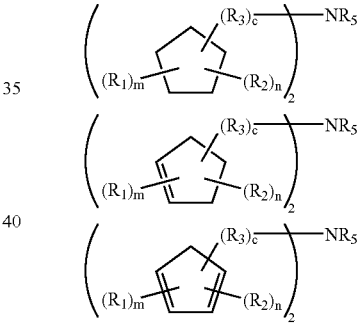

wherein c is any integer, such as 0, 1, 2, 3, 4, 5, 6, 7, 8, 9, or 10; m and n can be zero or any positive integers. Preferably, the sum of m and n should be less than 5, although compounds with m+n exceeding five are also suitable in embodiments of the invention. $R_1$, $R_2$, $R_3$, and $R_5$ are individually a hydrocarbyl group, which may or may not include a polar group; $R_5$ may also be hydrogen.

In addition, oligomers of cyclopentanes, cyclopentenes, and cyclopentadienes can also be used in embodiments of the invention, and they may be represented by the following formulas:

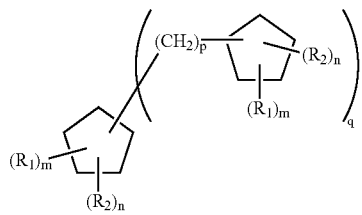

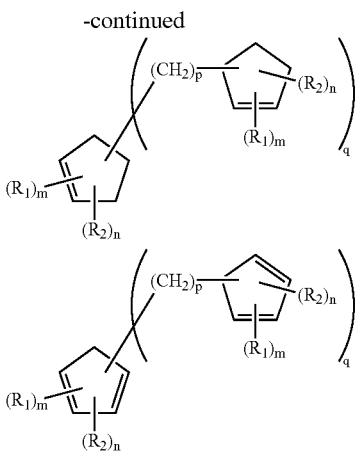

wherein p=1, 2, 3, . . . , or 10; q=1, 2, 3, . . . , or 10; m and n can be zero or any positive integers; preferably, the sum of m and n should be less than 5, although compounds with m+n exceeding five are also suitable in embodiments of the invention. $R_1$ and $R_2$ are individually a hydrocarbyl group, which may or may not include a polar group.

In addition, a cyclopentane, cyclopentene, or cyclopentadiene which includes a dimeric ester linkage may be represented by the following formulas:

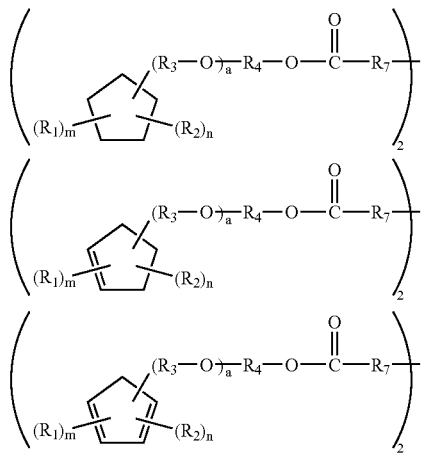

wherein a is any integer, such as 0, 1, 2, 3, 4, 5, 6, 7, 8, 9, or 10; m and n can be zero or any positive integers. Preferably, the sum of m and n should be less than 5, although compounds with m+n exceeding five are also suitable in embodiments of the invention. $R_1$, $R_2$, $R_3$, and $R_4$ are individually a hydrocarbyl group, which may or may not include a polar group; $R_7$ is a hydrocarbyl group from $C_1$ to $C_{20}$.

A cyclopentane, cyclopentene, or cyclopentadiene which includes a dimer secondary amide may also be used and may be represented by the following formulas:

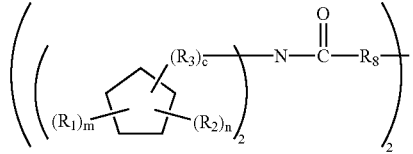

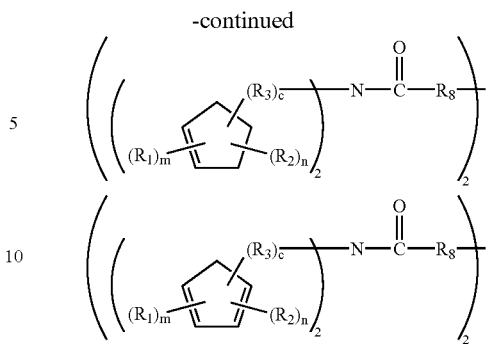

wherein c is any integer, such as 0, 1, 2, 3, 4, 5, 6, 7, 8, 9, or 10; m and n can be zero or any positive integers. Preferably, the sum of m and n should be less than 5, although compounds with m+n exceeding five are also suitable in embodiments of the invention. $R_1$, $R_2$ and $R_3$ are individually a hydrocarbyl group, which may or may not include a polar group; $R_8$ is a hydrocarbyl group from $C_1$ to $C_{20}$.

A cyclopentane, cyclopentene, or cyclopentadiene which includes a dimeric primary amide may also be used and may be represented by the following formulas:

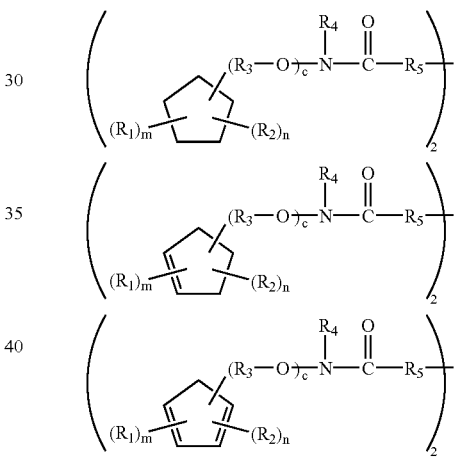

wherein c is any integer, such as 0, 1, 2, 3, 4, 5, 6, 7, 8, 9, or 10; m and n can be zero or any positive integers. Preferably, the sum of m and n should be less than 5, although compounds with m+n exceeding five are also suitable in embodiments of the invention. $R_1$, $R_2$, $R_3$, and $R_4$ are individually a hydrocarbyl group, which may or may not include a polar group; $R_4$ may also be hydrogen; $R_5$ is a hydrocarbyl group from $C_1$ to $C_{20}$.

Finally, Diels-Alder derivatives may also be used, and they may be represented by the following formulas:

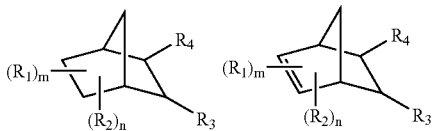

wherein m and n can be zero or any positive integers; preferably, the sum of m and n should be less than 5, although compounds with m+n exceeding five are also suitable in embodiments of the invention. $R_1$ and $R_2$ are individually a hydrocarbyl group, which may or may not include a polar group; $R_3$ and $R_4$ may be a hydrocarbyl, carboxylic acid, carboxylic ester, hydroxy, nitrile, or carboxylic amide. Additional suitable Diels-Alder derivatives that may be used in embodiments of the invention are disclosed by European Patent Applications No. 0 613 886 A1 and No. 0 613 887 A1, both of which were filed on Feb. 25, 1994. The disclosures of these patent applications are incorporated herein by reference in their entirety.

Synthesis of Selected Lubricants

1. Preparation of 3-[tris(2-octyldodecyl) cyclopentadienyl] propionitrile

Tris(2-octyldodecyl)cyclopentadiene (18.12 grams, 20 m mol) was placed in a 3-necked round bottom flask equipped with an additional funnel, a gas inlet adapter, and a septum. After flushing with dried $N_2$ for 2 minutes, 50 ml of dried THF (distilled over K) was added. The solution was cooled in dry ice/acetone bath, followed by injection of 8.4 M n-butyl lithium in hexane solution (2.40 ml; 20 m mol). The dry ice/acetone bath was removed, and the resulting dark red solution was stirred at room temperature for 1 hour, followed by cooling in dry ice/acetone bath. 3-Bromopropionitrile (2.70 grams, 20 m mol) in 10 ml dried THF solution was then dropwise added from the additional funnel. After the addition, the reaction solution was stirred at room temperature for another 3 hours. The reaction was slowly quenched with 10 ml water. The organic layer was separated, and the aqueous layer was extracted with 50 ml hexane. The organic layers were combined, dried over $MgSO_4$, filtered, and rota-vaporized to give 19.6 grams of yellow liquid. The crude reaction product was purified by column chromatography on $SiO_2$ eluting with 5% ethyl acetate/hexane. The unreacted tris(2-octyldodecyl)cyclopentadiene (3.66 grams) was recovered and the title compound (12.83 grams) was isolated. FTIR: 2248 $cm^{-1}$ (C≡N); $^{13}C$ NMR (4 isomers): 152.5–129.1 ppm (C=C), 120.8–119.6 ppm (4 peaks; C≡N), 59.5 ppm, 56.9 ppm, 51.3 ppm, 41.1 ppm, 39.5–26.4 ppm, 22.7 ppm, 14.1 ppm.

2. Preparation of Bis-[tris(2-octyldodecyl)cyclopentyl 3-propyl] amine

3-[Tris(2-octyldodecyl)cyclopentadienyl] propionitrile (5.24 grams), palladium 10 wt % on activated carbon (0.1 gram), and 250 ml of heptane were placed in a 500 ml Zipper Clave reactor. Hydrogen was introduced. The hydrogenation was maintained at 700 psi $H_2$, 130° C. for 24 hours. After cooling at room temperature, the catalyst was filtered off, and the solvent was rota-vaporized. The yellow liquid product was chromatographed on $SiO_2$ eluting with 5% ethyl acetate/hexane to give the title compound as a pale yellow viscous liquid (4.33 grams) having a kinematic viscosity of 40 cSt at 100° C., 380 cSt at 40° C., a viscosity index of 155, and $R_f$ (TLC on $SiO_2$, 5% ethyl acetate/hexane) of 0.58. FTIR: 1465 $cm^{-1}$, 1376 $cm^{-1}$, 1307 $cm^{-1}$, 1130 $cm^{-1}$, 721 $cm^{-1}$.

3. Preparation of 3-[tris(2-octyldodecyl)cyclopentyl] propyl amine

To a stirring solution of 3-[tris(2-octyldodecyl) cyclopentadienyl] propionitrile (8.38 grams; 9.23 m mol) in 20 ml of dried THF was slowly added 1 M lithium alumina hydride in THF solution (9.3 ml) at 0° C. After the addition, the ice bath was removed. The reaction was further stirred at room temperature for 2 hours. The reaction was slowly quenched with 10 ml of water. The reaction mixture solution was extracted with hexane (2×20 ml). The organic layer was dried over $MgSO_4$, filtered, and rota-vaporized to yield 10.31 grams. The crude product without purification was hydrogenated in the same manner described in synthesis 2. After the catalyst was filtered and rota-vaporized, the hydrogenated product was further purified by column chromatography on $SiO_2$ eluting with 40% ethyl acetate/hexane to yield 5.21 grams of the title compound. FTIR: 3392 $cm^{-1}$, 1618 $cm^{-1}$, 1074 $cm^{-1}$, 786 $cm^{-1}$, and 721 $cm^{-1}$ (no C≡N at 2248 $cm^{-1}$ was present). $^1H$ NMR: δ 2.66 (2H); δ 1.28; and δ 0.90 (t, 18H).

4. Preparation of 2-[2-tris(2-octyldodecyl) cyclopentadienyl ethoxy] ethanol

The hydroxyl group of 2-(2-chchloethoxy)ethanol was protected with 3,4-dihydro-2H-pyran, according to known procedure, to form the corresponding tetrahydropyranyl derivative in 96% yield. The reaction was carried out in methylene in the presence of catalytic amount of p-toluenesulfonic acid.

Tris(2-octyldodecyl)cyclopentadiene (18.12 grams, 20 m mol) was placed in a 3-necked round bottom flask equipped with an additional funnel, a gas inlet adapter, and a septum. After flashing with dried $N_2$ for 2 minutes, 50 ml of dried THF was added. The solution was cooled in a dry ice/acetone bath, followed by injecting 8.4 M n-butyl lithium in hexane solution (2.40 ml; 20 m mol). The dry ice/acetone bath was removed, and the resulting dark red solution was stirred at room temperature for 1 hour, followed by cooling in a dry ice/acetone bath. The above tetrahydropyranyl derivative of 2-(2-chchloethoxy)ethanol (4.45 grams, 20 m mol) in 10 ml dried THF was then dropwise added from the additional funnel. After the addition, the reaction solution was stirred overnight at room temperature under $N_2$. The reaction was slowly quenched with 20 ml water. The organic layer was separated, and the aqueous layer was extracted with 50 ml hexane. The organic layers were combined, dried over $MgSO_4$, filtered, and rota-vaporized to give 21.65 grams of liquid. To the liquid was added 20 ml of methylene dichloride and 0.2 ml of concentrated HCl to de-protect the hydroxy group. The reaction mixture was stirred overnight, followed by aqueous work-up to give 19.27 grams of a crude product. The title compound (16.90 grams) was obtained after purification by column chromatography on $SiO_2$, eluting with 5% ethyl acetate/hexane. FTIR: 3471 $cm^{-1}$, 3050 $cm^{-1}$, 1647 $cm^{-1}$, 1618 $cm^-$, 1058 $cm^{-1}$. $^{13}C$ NMR (2 isomers): 150.7 ppm, 148.4 ppm, 145.1 ppm, 142.6 ppm, 139.3 ppm, 126.7 ppm, 122.9 ppm, 121.9 ppm, 71.8 ppm, 68.8 ppm, 61.9 ppm, 47.8–26.5 ppm, 22.7 ppm and 14.1 ppm.

5. Preparation of 2-[2-tris(2-octyldodecyl)cyclopentyl]-ethoxy ethanol

The hydrogenation of 2-[2-tris(2-octyldodecyl) cyclopentadienyl]-ethoxy ethanol was carried out in a similar manner as described in synthesis 2, except the catalyst used was rhodium on alumina.

2-[2-tris(2-octyldodecyl)cyclopentadienyl]-ethoxy ethanol (20 grams), rhodium (5% Rh) on alumina (1 gram), and 250 ml of heptane were placed in a 500 ml Zipper Clave reactor. The hydrogenation was maintained at 950 psi $H_2$ and 280° C. for 24 hours. The title compound was further purified by column chromatography on $SiO_2$, eluting with 5% ethyl acetate/hexane, to give 18.59 gram of colorless liquid. FTIR: 3471 $cm^{-1}$, 1120 $cm^{-1}$, 1058 $cm^{-1}$, 890 $cm^{-1}$, 721 $cm^{-1}$. $^1H$ NMR: d 3.70 (1H), d 3.52 (1H), d 3.46 (1H), d 1.25, d 0.87. $^{13}C$ NMR: 71.8 ppm, 70.5 ppm, 61.9 ppm, 52.8–33.7 ppm, 31.9 ppm, 30.3 ppm, 29.8 ppm, 29.5 ppm, 26.7 ppm, 22.7 ppm, and 14.1 ppm.

6. Preparation of 3,5-di-tertiary-butyl 4-hydroxy benzoic ester of [2-tris-(2-octyldodecyl) cyclopentyl]-ethoxy ethanol 2-[2-tris(2-octyldodecyl)cyclopentyl]-ethoxy ethanol (8.0 grams, 8.35 m mol), 3,5-di-tert-butyl-4-hydroxybenzoic acid (2.94 grams, 12.6 m mol), and a catalytic amount of p-toluenesulfonic acid in 60 ml toluene were refluxed in a Dean-Stark trap. The reaction was monitored by TLC until all $^2$-[$^2$-tris(2-octyldodecyl)cyclopentyl]-ethoxy ethanol was consumed. It took 4 days to complete the reaction. The reaction solution was washed with 1M aqueous $K_2CO_3$ (2×20 ml). After being dried, filtered, and rota-vaporized, the crude reaction product was chromatographed on $SiO_2$, eluting with 3% ethyl acetate/hexane to yield about 9.87 grams of the pure title compound. The pure title compound was characterized by the following: FTIR: 3635 cm$^{-1}$, 1718 cm$^{-1}$, 1600 cm$^{-1}$. $^1$H NMR: d 7.92 (s, 2H), d 5.63 (s, 1H), d 4.44 (t, 2H), d 3.74 (t, 2H), d 3.53 (m, 2H), d 1.44 (s, 18H), d 1.22 ( br. s.), d 0.91 (t, 18H). $^{13}$C NMR: 167 ppm, 158.2 ppm, 135.6 ppm, 127.2 ppm, 121.2 ppm, 68.1 ppm, 64.0 ppm, 45.1 ppm, 34.3 ppm, 31.9 ppm, 30.2 ppm, 30.1 ppm, 29.8 ppm, 29.4 ppm, 22.7 ppm, 14.1 ppm.

7. Preparation of Di-(n-decyl)cyclopentane crosslinked by —$(CH_2)_{10}$-groups

In a one-liter three-necked flask fitted with a mechanical stirrer and a Soxhlet extractor packed with 3A molecular sieves (about 15 g) and topped with a condenser, 25.1 g of di-(n-decyl)cyclopentadiene (73 mmol), 12.6 g of 1,10-decanediol (73 mmol), 5 g of KOH, and 250 g of triglyme were stirred and deoxygenated with a stream of nitrogen. The mixture was then heated to reflux under nitrogen for two hours. The mixture was cooled and washed with water to remove base and triglyme. The product was dried and hydrogenated over palladium on carbon. The resulting product was characterized by gel permeation chromatography to determine the molecular weight. The number average molecular weight was 1250, indicating that on average about 3 di(n-decyl)cyclopentadienes had been crosslinked. The weight average molecular weight of 2250 indicates that molecules containing a higher number of crosslinked di(n-decyl)cyclopentadienes were formed. The measured viscosity at 100°, 40 cSt, is consistent with these high molecular weights.

8. Preparation of Diester of [2-tris(2-octyldodecyl) cyclopentyl]-ethoxy ethanol with Sebacic Acid 2-[2-tris(2-octyldodecyl)cyclopentyl] ethoxy ethanol (9.98 grams, 10 mmol), sebacic acid (1.01 grams, 5 mmol), and a catalytic amount of p-toluenesulfonic acid in 100 ml toluene was refluxed in a Dean-Stark trap for 3 days. The reaction solution was washed with 1M aqueous $K_2CO_3$ (2×20 ml). After being dried, filtered, and rota-vaporized, the crude reaction product was chromatographed on $SiO_2$, eluting with 20% ethyl acetate/hexane. The pure title compound (3.57 grams) was obtained. FTIR: 1741 cm$^{-1}$. $^{13}$C NMR: 174 ppm, 68.5 ppm, 64 ppm.

9. Preparation of Dimer Secondary Amide of Bis[tris (2-octyldodecyl)cyclopentyl 3-propyl] amine with Sebacoyl Chloride Bis[tris (2-octyldodecyl)cyclopentyl 3-propyl] amine (3.0 grams, 1.56 mmol) was placed in a round-bottomed flask with a septum. After flushing with nitrogen for 5 minutes, toluene (5 ml) and pyridine (2.52 ml) were added from syringes, followed by sebacoyl chloride (3.74 ml or 0.5 grams, 0.78 mmol). The cloudy solution was stirred overnight under nitrogen. The white precipitate was filtered and the filtrate was washed with diluted aqueous HCl. After being dried, filtered, and rota-vaporized, the crude reaction product was chromatographed on $SiO_2$, eluting with 5% ethyl acetate/hexane. The pure title compound (2.32 grams) was obtained. FTIR: 1654 cm$^{-1}$ (secondary amide). $^{13}$C NMR: 174.3 ppm (C=O).

10. Preparation of Dimer Primary Amide of 3-[tris(2-octyldodecyl)cyclopentyl] propyl amine with Sebacoyl Chloride The same procedure as described in synthesis 9 was followed except 3-[tris(2-octyldodecyl)cyclopentyl] propyl amine (1.49 grams, 2 mmol), sebacoyl chloride (0.24 grams, 1 mmol), and pyridine (0.16 grams, 2 mmol) were used. After being chromatographed, the pure title compound (0.95 grams) was obtained. FTIR: 3301 cm$^{-1}$, 1648.9 cm$^{-1}$. $^{13}$C NMR: 175.8 ppm (C=O).

11. Preparation of perfluorononanoic ester of 2-[2-tris(2-octyldodecyl)cyclopentyl]-ethoxy ethanol 2-[2-tris(2-octyldodecyl)cyclopentyl ethoxy] ethanol (4.0 grams), perfluorononanoic acid (2.40 grams) and a trace of toluenesulfonic acid in 50 ml toluene were placed in a 100-mL round bottom flask equipped with a Dean-Stark trap. The reaction was refluxed under $N_2$ for overnight. Without aqueous work-up, the reaction was stripped off the solvent. The crude product was column chromatographed on silica gel, eluting with 2% ethyl acetate in hexane to give 4.51 grams (61% yield) of the title compound as a pale yellow liquid. FTIR: 1785 cm$^{-1}$ (strong); $^{13}$C NMR: 159 ppm (C=O), 100–120 ppm ($CF_2$); $^{19}$F NMR: −80.9 ppm (terminal $CF_3$), −118.8 ppm, −120.1 ppm, −123 ppm, and −126.3 ppm. The ratio of the peak at −80.9 ppm to the rest of peaks was 3:14.

12. Preparation of perfluorododecanoic ester of 2-[2-tris (2-octyldodecyl)cyclopentyl]-ethoxy ethanol The same procedure as described in synthesis 8 was followed except perfluorododecanoic acid was used instead of perfluorononanoic acid. 2-[2-tris(2-octyldodecyl) cyclopentyl ethoxy] ethanol (58.0 grams), perfluorododecanoic acid (42.8 grams) and a trace of toluenesulfonic acid in 200 ml toluene were refluxed under $N_2$ for 3 days. The crude product was purified by column chromatography to give 40.6 grams of the title compound. FTIR: 1785 cm$^{-1}$ (strong); $^{19}$F NMR: −81.2 ppm (terminal $CF_3$), −118.4 ppm, −121.9 ppm (the highest peak), −123.1 ppm, and −126.3 ppm. The ratio of the peak at −81.2 ppm to the rest of peaks was 3:20.

13. Preparation of perfluorohexadecanoic ester of 2-[2-tris(2-octyldodecyl) cyclopentyl]-ethoxy ethanol The same procedure as described in synthesis 8 was followed except perfluorohexadecanoic acid was used instead of perfluorononanoic acid. 2-[2-tris(2-octyldodecyl) cyclopentyl ethoxy] ethanol (3.94 grams), perfluorododecanoic acid (4.26 grams) and a trace of toluenesulfonic acid in 50 ml toluene were refluxed under $N_2$ for 3 days. The crude product was purified by column chromatography to give 3.01 grams of the title compound. On a TLC plate, the title compound had the same Rf as example 8. FTIR: 1785 cm$^-$(strong).

14. Preparation of perfluorooctadecanoic ester of 2-[2-tris (2-octyldodecyl)cyclopentyl]-ethoxy ethanol The same procedure as described in synthesis 8 was followed except perfluorooctadecanoic acid was used instead of perfluorononanoic acid. 2-[2-tris(2-octyldodecyl) cyclopentyl ethoxy] ethanol (3.0 grams), perfluorohexadecanoic acid (3.29 grams) and a trace of toluenesulfonic acid in 50 ml toluene were refluxed under $N_2$ for 3 days. The crude product was purified by column chromatography to give 1.75 grams of the title compound. On a TLC plate, the title compound had the same Rf as example 10. FTIR: 1785 cm$^{-1}$ (strong); $^{13}$C NMR: 159 ppm (C=O), 100–120 ppm (CF$_2$).

Magnetic Recording Medium

In accordance with embodiments of the invention, a magnetic recording medium includes: (1) a non-magnetic support; (2) a magnetic layer formed on the support; and (3) lubricant layer over the magnetic layer. The lubricant layer includes a compound selected from the group consisting of hydrocarbyl-substituted cyclopentane, hydrocarbyl-substituted cyclopentene, hydrocarbyl-substituted cyclopentadiene, and mixtures or derivatives thereof. Optionally, there may be a protective layer between the magnetic layer and the lubricant layer. In other words, some embodiments may include a protective layer while other embodiments may not include such a layer.

In some embodiments, the hydrocarbyl substituent on the cyclopentane, cyclopentene, and cyclopentadiene may be derivatized to include one or more polar groups, such as hydroxy, carboxylic acid, amine, carboxylic ester, carboxylic amide, phosphate, fluorine, and sulfur compounds. For example, hydroxylated, dihydroxylated, and polyhydroxylated derivatives are preferred. Carboxylic acid derivatives and their salts, amine derivatives, carboxylic ester derivatives, carboxylic amide derivatives, phosphate derivatives, and sulfur compounds derived from multiple-alkylated cyclopentadienes, multiple-alkylated cyclopentenes, and multiple-alkylated cyclopentanes also may be used. These derivative groups, e.g., polar groups, may be incorporated into a multiple-alkylated cyclopentadiene, cyclopentene, or cyclopentane by known chemistries of cyclopentadiene, alkene, diene, and alkane. For example, cyclopentadiene can be made to undergo Diels-Alder reactions and nucleophilic reactions to include derivative groups. These derivative groups may strengthen the bonding between the lubricant film and the surface beneath it.

In addition to a magnetic recording medium, a magnetic head for reading and writing information on the magnetic recording medium also is provided by embodiments of the invention. The magnetic head includes: (1) a head body; and (2) a lubricant layer over at least a portion of the head body. The lubricant layer includes a compound selected from the group consisting of hydrocarbyl-substituted cyclopentane, hydrocarbyl-substituted cyclopentene, hydrocarbyl-substituted cyclopentadiene, and mixtures or derivatives thereof. Similarly, the hydrocarbyl substituents may be derivatized to include one or more polar groups. A data storage/retrieval device may be constructed using either the magnetic head or the magnetic recording medium provided by embodiments of the invention.

Figure 2:
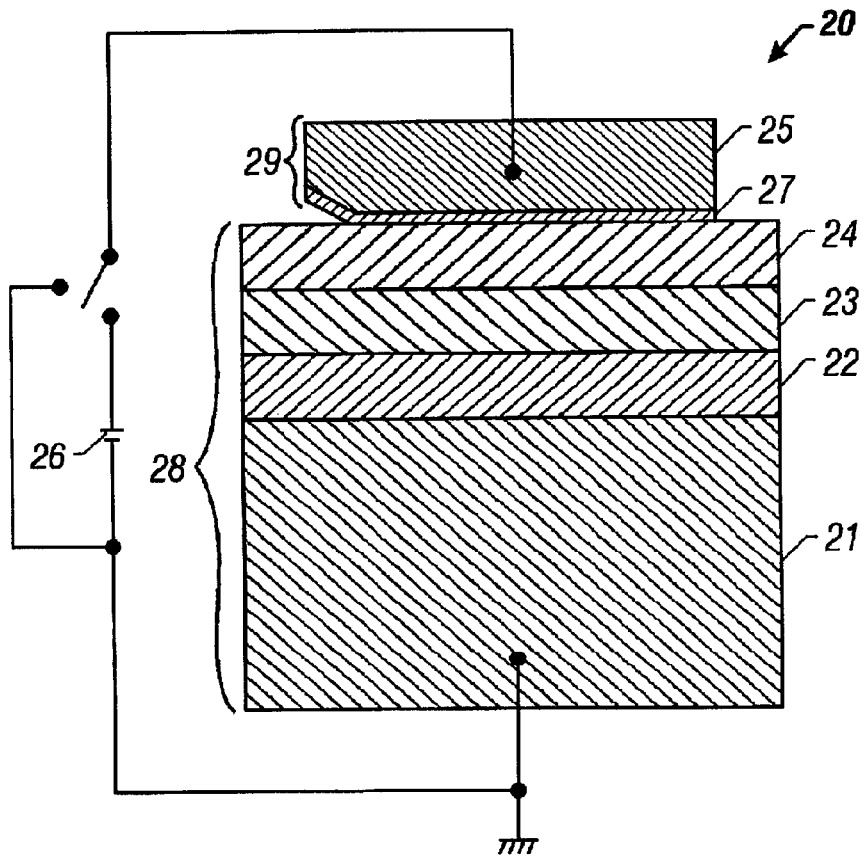
FIG. 2 is a cross-sectional view of a data storage/retrieval device in accordance with an embodiment of the invention.

FIG. 2 illustrates a cross-sectional view of a data storage/retrieval device manufactured in accordance with one embodiment of the invention. It should be understood that the data storage/retrieval device maybe used to manufacture computers audio/video equipment, and the like. Typically, a computer includes a central processing unit ("CPU"), a monitor, a keyboard, and a disk drive connected to the CPU. Other components suitable for constructing a computer are known in the art. For example, U.S. Pat. No. 4,620,275 discloses a computer, and the disclosure of this patent is incorporated by reference herein in its entirety.

Referring to FIG. 2, a data storage/retrieval device 20 includes a magnetic recording medium 28, a magnetic head 29, and a power supply 26, which is connected to the magnetic recording medium 28 and the magnetic head 29. The magnetic recording medium 28 is formed by coating a layer of magnetic material 22 on a substrate support 21. Preferably, the layer of magnetic material 22 is protected by a protective layer 23. The lubricant layer 24 is provided on the protective layer 23. The magnetic head 29 includes a body 25 for the head and an insulating layer 27 which is optional. In some embodiments, the magnetic head 29 is coated with a lubricant layer. To operate this data storage/retrieval device, a DC voltage from a power supply 26 preferably is applied across the support 21 and the magnetic head 29.

The magnetic recording medium in accordance with embodiments of the invention may be manufactured by the following method: (1) providing a non-magnetic support; (2) forming a magnetic layer on the support; and (3) forming a lubricant layer over the magnetic layer. The lubricant layer includes a compound selected from the group consisting of hydrocarbyl-substituted cyclopentane, hydrocarbyl-substituted cyclopentene, hydrocarbyl-substituted cyclopentadiene, and mixtures or derivatives thereof. Optionally, a protective layer may be formed between the magnetic layer and the lubricant layer.

Generally, any non-magnetic materials may be used as a substrate support. Suitable materials for the support include, but are not limited to, a metal such as an aluminum alloy, a titanium alloy, or a stainless steel alloy; plastic such as polyester, polyimide, polyamidoimide, polyethersulfone, polysulfone, aromatic polyether, an epoxy resin, a urea resin, a melamine resin, polycarbonate, a diallylphthalate resin, an acrylic resin, a phenolic resin, polyphenylenesulfide, polyphenyleneether, a polyacetal resin, polybutyreneterephthalate, a bismaleimidetriazine resin, a polyoxybenzylene resin, a polyphenylenesulfide; ceramics such as glass, silicon, germanium, alumina, silica, diamond, amorphous carbon, or graphite; and a metal such as an aluminum alloy coated with anodized aluminum, an Ni—P-plating film, Cr, Fe, Ni, stainless steel, Mo or W. It should be recognized that a non-magnetic support is not always necessary in manufacturing a magnetic medium.

Any magnetic materials maybe used to form the magnetic layer on the support. Suitable magnetic materials include, but are not limited to, an oxide such as Fe$_3$O$_4$, g-Fe$_2$O$_3$, barium ferrite, or CrO$_2$; a nitride such as Fe$_3$N$_4$; a carbide such as Fe$_5$C$_2$; a metal containing cobalt such as Co, CoNi, CoNiP, CoMnP, CoMnNiP, CoRe, CoPt, CoNiPt, CoCr, CoCrTa, CoNiRe, CoMnReP, CoFeCr, CoV, CoRu, CoOs, CoPtCr, CoPtV, CoRh, CoCrRh, CoNiMo, CoNiCr, CoNiW, or CoSm; a metal containing iron such as FeNd, FeMg, FeNd, FeAg, FePd, or FeTb; and a metal containing manganese such as MnAI or MnCuAL. It also is possible to use a resin prepared by mixing and dispersing fine particles of the above various magnetic materials.

Suitable materials for forming the protective layer between the magnetic layer and the lubricant layer include, but are not limited to, a silicon compound such as SiO$_2$, Si$_3$N$_4$, SiC, or a silicic acid polymer; a metal oxide such as Al$_2$O$_3$, CoO, Co$_3$O$_4$, Co$_2$O$_3$, a-Fe$_2$O$_3$, Cr$_2$O$_3$, CrO$_3$, TiO$_2$, ZrO$_2$, ZnO, PbO, NiO, MoO$_2$, or SnO$_2$; a metal sulfide such as MoS$_2$, WS$_2$, or TaS$_2$; a metal carbide such as TiC, ZrC, CrC, or TaC; a metal fluoride or graphite fluoride; a metal such as W, Cr, Ir, NiB, NiP, FeCr, NiCr, Sn, Pb, Zn, Tl, Au, Ag, Cu, Ga, Ru, Rb, Mn, Mo, Os, or Ta, or an alloy of each of these metals; a semiconductor such as Si, Ge, B, or C, (e.g., amorphous hydrogenated carbon, amorphous nitrogenated carbon, amorphous carbon, diamond-like carbon, or a mixture thereof, or graphite-like carbon or a mixture thereof); and plastic such as polytetrafluoroethylene, a phenolic resin, or polyimide.

Methods for forming these layers are known in the art. For example, these films may be formed by chemical vapor deposition, physical vapor deposition, electrochemical plating, electron-assisted deposition, ion-assisted deposition, and so on. Suitable materials for making the body of the magnetic head include, but are not limited to, an insulator such as quartz, glass, alumina, sapphire, ruby, diamond, or silicon; silicon carbide having conductivity, a sintered body such as alumina-titanium carbide; and a ceramics-based conductor, such as manganese-zinc ferrite or nickel-zinc ferrite. Optionally, a thin insulating film may be applied to the body of the magnetic head. The insulating film may include diamond-like carbon, $SiO_2$, or alumina. In some embodiments, the magnetic head is coated with a lubricant layer formed from a compound selected from the group consisting of hydrocarbyl-substituted cyclopentane, hydrocarbyl-substituted cyclopentene, hydrocarbyl-substituted cyclopentadiene, and mixtures or derivatives thereof.

The thickness of the lubricant layer containing the hydrocarbyl-substituted cyclopentane, hydrocarbyl-substituted cyclopentene, hydrocarbyl-substituted cyclopentadiene, and mixtures or derivatives thereof which is formed on the magnetic head may be a factor in influencing the performance of the disk drive and/or the durability of the lubricant layer. The desired thickness is based upon a variety of factors including, but not limited to, customer requirements and applications, the composition of the magnetic head, the composition of the lubricant layer, the existence of a protective layer and its composition. In some embodiments, the desired thickness of the lubricant layer ranges from about 5 Å to about 25 Å. In other embodiments, the desired thickness of the lubricant layer ranges from about 5 Å to about 15 Å.

The molecular weight of the compounds used in forming the lubricant layer on the magnetic head may also be a factor in influencing the performance of the disk drive and/or the durability of the lubricant layer. The desired molecular weight of the lubricants and optional additives which are used in forming the lubricant layer is based upon a variety of factors including, but not limited to, customer requirements and applications, the composition of the magnetic head, the materials used to form the lubricant layer. In some embodiments, the desired molecular weight of the compounds used in forming the lubricant layer ranges from about 300 g/mol to about 6000 g/mol. In other embodiments, the desired molecular weight of the compounds used in forming the lubricant layer ranges from about 500 g/mol to about 4000 g/mol.

While the cyclopentanes, cyclopentenes, and cyclopentadienes may be used alone in forming a lubricant layer, one or more additional lubricants and/or additives also may be used in combination with the cyclopentanes, cyclopentenes, and cyclopentadienes described herein provided the additional lubricants and/or additives do not adversely affect the performance of the magnetic recording media.

Suitable additional lubricants include, but are not limited to, metallic soaps; fatty acids; amides; fatty acid esters; higher aliphatic alcohols; monoalkyl phosphates; dialkyl phosphates, trialkyl phosphates, paraffins, silicone oils; animal or vegetable oils; mineral oils; higher aliphatic amines; inorganic fine powders such as graphite, silica, molybdenum disulfide, and tungsten disulfide; resin fine powders such as polyethylene, polypropylene, polyvinyl chloride, ethylene vinyl chloride copolymer, and polytetrafluoroethylene; α-olefin polymers; and unsaturated aliphatic hydrocarbons which are liquid at room temperature.

Suitable additives for use in embodiments of the invention will not adversely affect the performance of the magnetic recording media. Suitable additives include, but are not limited to, antioxidants, antiwear additives, friction modifier additives, and combinations thereof. The additives for use in embodiments of the invention may be of the ash producing or ashless type. While an additive may be described herein as an antioxidant, an antiwear agent, or a friction modifier, many of the additives described herein have properties of one, both or all three components and provide the effects of one, both, or all three. For example, a single additive, while listed as an antioxidant, may, in some circumstances, also act as an antiwear agent and/or a friction modifier component. The type of additive which is selected depends on a variety of factors including, but not limited to, customer requirements and applications, the composition of the magnetic head, the physical properties of the additives, the physical properties of the other compounds used in forming the lubricant layer, the synergism between the additives and the cyclopentanes, cyclopentenes, and cyclopentadienes. Other suitable additives are cyclic phosphazenes such as mixtures of fluorinated phenoxy-substituted cyclic phosphazenes or mixtures of fluoroalkoxy substituted cyclic phosphazenes.

As used herein, the term "antioxidant" is hereby defined to be a material which inhibits oxidation or degradation of another material or acts as a free radical scavenger. The term "oxidation" as used herein is defined to mean any reaction in which electrons are transferred. Antioxidant materials useful in the present invention generally reduce the tendency of hydrocarbons to deteriorate in service.

The antioxidant(s) which may be used in the lubricant composition are not particularly limited and may be any conventional antioxidant(s) known to those skilled in the art. Examples of antioxidant additives which may be used include, but are not limited to, hydroxy compounds such as hydroxy-substituted aromatic groups such as phenols, hindered phenols, and sulfurized phenols; nitrogen based compounds such as amines, high molecular weight ether amine antioxidants, and hindered amine light stabilizers; phosphorous based antioxidants such as phosphites, phosphite esters, phosphinates, phosphonites, phosphorothioates, phosphorothiolothionates, phosphorothionates, phosphorodithioate, and fluoro-phosphonite compositions; sulfur based antioxidants such as sulfides, sulfurized olefins, sulfurized fatty oils, and mixtures of sulfurized fatty oils and olefins; thioethers; thioacetals; thiocarbamates; boron based antioxidants; ashless antioxidants; metal chelating agents; ethoxyquin; copper compounds; molybdenum compounds; and combinations thereof. A hindered phenolic antioxidant is a phenol in which the two positions on the phenolic ring ortho to —OH are occupied by bulky substitutents. One example of a commercially available hindered phenol is BHT, butylated hydroxytoluene, which is 2,6-di-(t-butyl)-4-methylphenol.

Other suitable phenolic antioxidants include, but are not limited to, acylaminophenols, alkylated hydroquinones, alkylated phenols, alkylidene bisphenols, alkylthiomethylphenols, benzyl compounds, benzylphosphonates, esters and amides of hindered phenol-substituted alkanoic acids, hydroquinones, alkylated hydroquinones, hydroxybenzyl aromatics, hydroxybenzylated malonates, hydroxylated thiodiphenyl ethers, methylene bridged alkylphenols, O,S, and S-benzyl compounds, oil soluble phenolic compounds, tocophenols, triazines, unbridged phenols, and combinations thereof. Where a phenolic antioxidant is used, the phenol may optionally include esters, sulfur, and/or sulfurized esters. In addition, the ester group may be substituted in the para position on the phenol ring. Preferred phenols include, but are not limited to, diesters of 3,5-di-t-butyl-4-hydroxyhydrocinnamic acid with 1,6-hexanediol.

Non-limiting examples of suitable phenolic antioxidants include 1,1,3-tris(5-t-butyl-4-hydroxy-2-methylphenyl)-3-n-dodecylmercaptobutane; 1,1-bis(5-t-butyl-4-hydroxy-2-methylphenyl)butane; 1,3,5-trimethyl-2,4,6-tris-(3,5-di-t-butyl-4-hydroxybenzyl)benzene; 1,3,5-tris-(3,5-di-t-butyl-4-hydroxybenzyl)isocyanurate; 1,3,5-tris(3,5-di-t-butyl-4-hydroxybenzyl)2,4,6-trimethylbenzene; 1,3,5-tris(4-t-butyl-3-hydroxy-2,6,dimethylbenzyl)isocyanurate; 1,3,5-tris-(4-t-butyl-3-hydroxy-2,6-dimethylbenzyl)-1,3,5-triazine-2,4,6-(1H, 3H, 5H)trione; 1-[2-{3-(3,5-di-t-butyl-4-hydroxyphenyl)propionyloxy}ethyl]-4-{3-(3,5-di-t-butyl-4-hydroxyphenyl)propionyloxy}-2,2,6,6-tetramethylpiperidine; 2-methyl-6-t-butyl-phenol; 2-(α-methylcyclohexyl)-4,6-dimethylphenol; 2,2'-ethylidenebis (6-t-butyl-4-isobutylphenol); 2,2'-methylenebis(4,6-di-t-butylphenol); 2,2'-methylenebis(4-methyl-6-cyclohexylphenol); 2,2'-methylenebis(4-methyl-6-t-butylphenol); 2,2'-methylenebis(6-nonyl-4-methylphenol); 2,2'-methylenebis(6-t-butyl-4-ethylphenol); 2,2'-methylenebis(6-t-butyl-4-methylphenol); 2,2'-methylenebis{(6-α-methylbenzyl)-4-nonylphenol}; 2,2'-methylenebis{4-methyl-6-(α-methylcyclohexyl)phenol}; 2,2'-methylenebis{6-(",α-dimethylbenzyl)-4-nonylphenol}; 2,2'-methylidenebis(4,6-di-t-butylphenol); 2,2'-thiobis(4-octylphenol); 2,2'-thiobis(6-t-butyl-4-methylphenol); 2,4,6-tricyclohexylphenol; 2,4,6-tri-t-butylphenol; 2,4-bis-octylmercapto-6-(3,5-di-t-butyl-4-hydroxyaniline)-s-triazine; 2,4-dimethyl-6-t-butylphenol; 2,5-di-t-amyl-hydroquinone; 2,5-di-t-butyl-hydroquinone; 2,6-di(3-t-butyl-5-methyl-2-hydroxybenzyl)-4-methylphenol; 2,6-dicyclopentyl-4-methylphenol; 2,6-di-isopropylphenol; 2,6-dioctadecyl-4-methylphenol; 2,6-di-phenyl-4-octadecyloxyphenol; 2,6-di-styryl-4-nonylphenol; 2,6-di-t-butyl-4-ethylphenol; 2,6-di-t-butyl-4-isobutylphenol; 2,6-di-t-butyl-4-methoxymethylphenol; 2,6-di-t-butyl-4-methylphenol; 2,6-di-t-butyl-4-n-butylphenol; 2,6-di-t-butylphenol; 2,6-ditertiarybutylphenol; 2-methyl-6-styrylphenol; 2-methyl-6-t-butylphenol; 2-t-butyl-4,6-dimethylphenol; 2-t-butylphenol; esters of 3,5-di-t-butyl-4-hydroxybenzylmercaptoacetic acid; esters of 3,5-di-t-butyl-4-hydroxybenzylphosphonic acid; esters of 3,5-di-t-butyl-4-hydroxybenzylphosphonic acid mono-ethyl ester calcium salt; 3,9-bis-[2-{3-(3-t-butyl-4-hydroxy-5-methylphenyl) propionyloxy}-1,1-dimethylethyl]-2,4,8,10-tetraoxaspiro{5,5}undecane; 3,5-tris(4-t-butyl-3-hydroxy-2, 6-dimethylbenzyl)isocyanuarate; 4-(N,N-dimethylaminomethyl)-2,6-di-t-butylphenol; 4,4'-methylene bis-(2,6-6-ditertiary butyl phenol); 4,4'-methylene-bis (2,6-di-t-butyl phenol); 4,4'-methylenebis(2,6-di-t-butylphenol); 4,4'-methylenebis(2-t-amyl-o-cresol); 4,4'-methylenebis(4, 6-di-t-butylphenol); 4,4'-methylenebis(6-t-butyl-2-methylphenol); 4,4'-methylenebis(6-t-butyl-o-cresol); 4,4'-thiobis(6-t-butyl-2-methylphenol); 4,4'-thiobis(6-t-butyl-3-methylphenol); 4-ethyl-2,6-di-t-butylphenol; 4-hydroxylauric acid anilide; 4-hydroxystearic acid anilide; 4-methyl-2,6-di-t-butylphenol; bis(4-t-butyl-3-hydroxy-2,6-dimethylbenzyl)dithioterephthalate; di(3,5-di-t-butyl-4-hydroxybenzyl)sulfide; di(3-t-butyl-4-hydroxy-5-methylphenyl)dicyclopentadiene; di{2-(3'-t-butyl-2'-hydroxy-5'-methylbenzyl)6-t-butyl-4-methylphenyl}terephthalate; esters of 3,5-di-t-butyl-4-hydroxyphenylacetic acid; esters of β-(3,5-dicyclohexyl-4-hydroxyphenyl)-propionic acid; ethylene glycol bis{3,3-bis (3'-t-butyl-4'-hydroxyphenyl)butyrate}; N-(3,5-di-t-butyl-4-hydroxyphenyl)carbamic acid octyl ester; n-octadecyl-3-(3, 5-di-t-butyl-4-hydroxyphenyl)propionate; octadecyl 3,5-di-t-butyl-4-hydroxyhydrocinnamate; o-t-butylphenol; tetrakis [methylene (3,5-di-t-butyl-4-hydroxylhydrocinnamate)] methane; tetrakis-{methylene-3-(3,5-di-t-butyl-4-hydroxyphenyl)propionate}methane; thiodiethylbenebis-(3, 5-di-t-butyl-4-hydroxy)hydrocinnamate; 4-methyl-2,6-di-t-butylphenol; esters of beta-(3,5-di-t-butyl-4-hydroxyphenyl)propionic acid with mono- or polyhydric alcohols such as methanol, octadecanol, 1,6-hexanediol, neopentyl glycol, thiodiethylene glycol, diethylene glycol, triethylene glycol, pentaerythritol, tris(hydroxyethyl) isocyanaurate, and di(hydroxyethyl)oxalic acid diamide; esters of β-(5-t-butyl-4-hydroxy-3-methylphenyl)propionic acid with mono- or polyhydric alcohols such as methanol, octadecanol, 1,6-hexanediol, neopentyl glycol, thiodiethylene glycol, diethylene glycol, triethylene glycol, pentaerythritol, tris(hydroxyethyl)isocyanaurate, and di(hydroxyethyl)oxalic acid diamide; and amides of β-(3,5-di-t-butyl-4-hydroxyphenyl-(propionic acid) such as N,N'-di-(3,5-di-t-butyl-4-hydroxyphenyl-proprionyl) hexamethylenediamine, N,N'-di(3,5-di-t-butyl-4-hydroxyphenypropionyl) trimethylenediamine, and N,N'-di-(3,5-di-tert-butyl-4-hydroxyphenylpropionyl)hydrazine. It is contemplated that the phenols described above may optionally include one or more alkyl substituents. Examples of suitable alkyl substituents include, but are not limited to, methyl, ethyl, propyl, isopropyl, t-butyl, n-butyl, pentyl, t-pentyl, hexyl, heptyl, n-octyl, t-octyl, nonyl, decyl, dodecyl, and styryl.

Examples of suitable sulfurized phenolic antioxidants include, but are not limited to, hindered sulfur-bridged phenols including those having a branched alkyl group on the alpha carbon atom, hindered bisphenols, oil soluble phenolic compounds, thiobisphenols, tert-butylphenols, and combinations thereof. Preferred sulfurized phenols include, but are not limited to the following compounds: 4,4'-thiobis (2,6-di-t-butylphenol); 4,4'-dithiobis(2,6-di-t-butylphenol); 4,4'-thiobis(2-t-butyl-6-methylphenol); 4,4'-dithiobis(2-t-butyl-6-methylphenol); 4,4'-thiobis(2-t-butyl-5-methylphenol); and combinations thereof.

Amine antioxidants generally improve the thermal-oxidative stability of lubricants. Suitable amine antioxidants include aromatic amines such as secondary aromatic amines and hindered aromatic amines.

Non-limiting examples of suitable amine antioxidants include: alkylated diphenylamines; alkylated phenyl-α-naphthylamines; alkylated polyhydroxy benzenoid compounds; aminoalkylphenothiazines; aminoguanidines; anthranilamide compounds; anthranilic acid esters; aromatic amines and substituted benzophenones; aromatic triazoles; bis-1,3-alkylamino-2-propanol; di-(4-methoxyphenyl) amines; di[4-(1',3'-dimethylbutyl)phenyl]amines; dialkylated diphenylamines; diarylamines; dibenzazepine compounds; diheptyldiphenylamines; dimethyl octadecylphosphonate-arylimino di-alkanol copolymers; dioctyldiphenylamines; diphenylamines including alkyl-diphenylamines having one or more alkyl substituents (branched or unbranched); di-t-butyl-4-dimethylaminomethylphenol; fluorinated aromatic amines; heptyldiphenylamines; isoindoline compounds; methyl-styryldiphenylamines; mixed butyl/octyl alkylated diphenylamines; mixed butyl/styryl alkylated diphenylamines; mixed ethyl/methylstyryl alkylated diphenylamines; mixed ethyl/nonyl alkylated diphenylamines; mixed octyl/styryl alkylated diphenylamines; mono- and dialkylated t-butyl-t-octyldiphenylamines; mono- and/or di-(α-methylstyryl) diphenylamines; mono- and/or di-butyldiphenylamines; mono- and/or di-nonyldiphenylamines; mono- and/or di-octyldiphenylamines; mono- and/or di-styryldiphenylamines;-(1,3-dimethylbutyl)-N'-phenyl-p-phenylenediamine; (-methylpentyl)-N'-phenyl-p-phenylenediamine; N,N,N'N'-tetramethyl-4,4'-diaminophenylmethane; N,N'dimethyl-N,N'-di-sec-butyl-p-phenyenediamine diphenylamine; N,N'-di-sec-butyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N,N'-di-(naphthyl-2)-p-phenylenediamine; N,N'-diisopropyl-p-phenylenediamine; N,N'-diphenyl-p-phenylenediamine; N-alkylated phenylenediamines; N-cyclohexyl-N'-phenyl-p-phenylenediamine; -isopropyl-N'-phenyl-p-phenylenediamine; N-nitro phenylhydroxylamines; nonyldiphenylamines; -phenyl-1,2-phenylenediamines; -phenyl-1,4-phenylenediamines; -phenyl-1-naphthylamines; -phenyl-2-naphthylamines; -phenyl-p-phenylenediamines; -substituted phenothiazines and triazines; octyl alkylated phenyl-alphanaphthylamines; octylated diphenylamines; oil soluble amine antioxidants; peroxide-treated phenothiazines; phenothiazines; phenyl-β-naphthylamines including alkyl- or aralkyl-substituted phenyl-β-naphthylamines containing one or more alkyl or aralkyl groups each having up to about 16 carbon atoms; phenyl-substituted and phenylene-substituted amines; phenyl-α-naphthylamines including alkyl- or aralkyl-substituted phenyl-α-naphthylamines containing one or more alkyl or aralkyl groups each having up to about 16 carbon atoms; phosphinodithioic acid-vinyl carboxylate adducts; phosphorodithioate ester-aldehyde reaction products; phosphorodithioate-alkylene oxide reaction products; silyl esters of terephthalic acid; substituted benzo-diazoborole; substituted indans; t-octylated-phenyl-1-naphthylamino; trialkylated diphenylamines; α-methyl styrenated aromatic amines; (o-tolyl) biguanide; 1,2-di(phenylamino)propane; 1,2-di[(2-methylphenyl)amino]ethane; 2,4'-diaminodiphenylmethane; 3-hydroxydiphenylamines; 3-tertiary alkyl-substituted phenothiazines; 4-(p-toluenesulfonamido)diphenylamines; 4,4'-diaminophenylmethanes; 4-alkylphenyl-1-alkyl-2-naphthylamines; 4-butyrylaminophenols; 4-dodecanoylaminophenols; 4-hydroxydiphenylamines; 4-isopropoxydiphenylamines; 4-n-butylaminophenols; 4-nonanoylaminophenols; 4-octadecanoylaminophenols; and combinations thereof.

It is contemplated that the amines described above may optionally include one or more alkyl substituents. Examples of suitable alkyl substituents include, but are not limited to, methyl, ethyl, propyl, isopropyl, t-butyl, n-butyl, pentyl, t-pentyl, hexyl, heptyl, n-octyl, t-octyl, nonyl, decyl, dodecyl, and styryl. Nonlimiting examples of commercially available amine antioxidants include Irganox® L06 and Irganox® L57 available from Ciba Geigy Specialty Chemicals.

In some embodiments, high molecular weight ether amine antioxidant additives may be used. Suitable high molecular weight ether amine antioxidants include, but are not limited to, N-hydrocarboxyloxypropyl-1,3-diaminopropane; hydrocarboxylpropylamine; and polyoxyalkyleneamine.

Blends of hindered phenolic antioxidants and amine antioxidants may also be used as additives in the lubricant layer. Examples of commercially available blends of hindered phenolic antioxidants and amine antioxidants include Irganox® L64, Irganox® 74, Irganox® L34, and Irganox® 150 available from Ciba Geigy Specialty Chemicals.

Examples of suitable phosphorous based antioxidants include, but are not limited to, dihydrocarbyl dithiophosphates, fluorophosphonites, phosphinates, phosphite esters, phosphates such as oil soluble organophosphates, phosphites such as oil soluble organophosphites, phosphonites, phosphorodithioate, phosphorothioates, phosphorous esters, oil soluble organo dithiophosphates, metal thiophosphates and dithiophosphates, metal salts of dihydrocarbyl dithiophosphoric acids, metal phosphorodithioates, and combinations thereof. Preferred phosphorous based antioxidants include, but are not limited to, Vanlube® 727 and Vanlube® 7611 (a methylene bis(dialkylthiocarbamate)) available from R. T. Vanderbilt Company, Inc. and Irgalube® 63 (a dialkyl dithiophosphate) available from Ciba Geigy Specialty Chemicals.

Examples of suitable phosphorous based antioxidants include, but are not limited to, the following compounds: 2,2',2α-nitro[triethyl-tris(3,3',5,5'-tetra-t-butyl-1,1'-biphenyl-2,2'-diyl)]phosphite; 2,2'-ethylidenebis-(4,6-di-t-butylphenyl)-fluorophosphonite; tris[2,4-di-t-butylphenyl] phosphite; bis(2,4-di-t-butylphenyl)pentaerythritol-diphosphite; bis[2,4-di-t-butyl]pentaerythritol diphosphite); dithiophosporic ester-alcohols; tetrakis (2,4-di-t-butylphenyl)-4,4'-biphenylenediphosphonite; tris(2,4-di-t-butylphenyl) phosphite; tris-(2-phenylphenyl)phosphite; tris-(2-t-butyl-4-methylphenyl)phosphite; tris-(2-t-butyl-5-methylphenyl)phosphite; tris-(4-phenylphenyl)phosphite; tris-(4-t-butylphenyl)phosphite; zinc dithiophosphates such as zinc dialkyldithiophosphate; alkyl- and aryl-(and mixed alkyl, aryl) substituted phosphates; alkyl- and aryl-(and mixed alkyl, aryl) substituted phosphites; and alkyl- and aryl-(and mixed alkyl, aryl) substituted dithiophosphates such as O,O,S-trialkyl dithiophosphates, O,O,S-triaryldithiophosphates and dithiophosphates having mixed substitution by alkyl and aryl groups; phosphorothionyl sulfides, phosphorus-containing silanes, polyphenylene sulfides, amine salts of phosphinic acid and quinone phosphates; and combinations thereof.

Nonlimiting examples of suitable sulfur based antioxidants include sulfides, dialkenyl sulfides, sulfurized olefins, sulfurized fatty acid esters, sulfurized aliphatic esters, diester sulfides, sulfurized fatty oils or mixtures of sulfurized fatty oils and olefins, sulfurized carboxylic acid esters, sulfurized ester olefins, sulfurized hydrocarbons, sulfurized alkyl-substituted hydroxyaromatic compounds, terpenes, and combinations thereof. Preferred sulfur based antioxidants include, but are not limited to, methylene bis (alkylsulfides), alkenyl sulfides, disulfides, polysulfides, and combinations thereof. Examples of dialkenyl sulfides include, but are not limited to, 6,6'-dithiobis(5-methyl-4-nonene), 2-butenyl monosulfide and disulfide, 2-methyl-2-butenyl monosulfide and disulfide, and combinations thereof. Examples of suitable sulfurized olefins include, but are not limited to, branched olefins, cyclic olefins, high molecular weight olefins such as those having an average molecular weight of 168 to 351 g/mole, isomerized α-olefins (structural and/or conformational isomers), α-olefins such as C4–C25 α-olefins, sulfurized olefins prepared by the reaction of an olefin or a lower molecular weight polyolefin derived therefrom with a sulfur-containing compound such as sulfur, sulfur monochloride and/or sulfur dichloride, hydrogen sulfide, isobutene, propylene and their dimers, trimers and tetramers, and mixtures thereof; and combinations thereof.

Examples of sulfurized fatty acid esters include those prepared by reacting sulfur, sulfur monochloride, and/or sulfur dichloride with an unsaturated fatty ester at elevated temperatures. Typical esters include C1 to C20 alkyl esters of C8 to C24 unsaturated fatty acids such as palmitoleic, oleic, ricinoleic, petroselic, vaccenic, linoleic, linolenic, oleostearic, licanic, etc. Specific examples of the fatty esters which can be sulfurized include lauryl talate, methyl oleate, ethyl oleate, lauryl oleate, cetyl oleate, cetyl linoleate, lauryl ricinoleate, oleolinoleate, oleostearate, and alkyl glycerides. The sulfurized organic compounds may also be sulfurized oils which may be prepared by treating natural or synthetic oils including mineral oils, lard oil, carboxylic acid esters derived from aliphatic alcohols and fatty acids or aliphatic carboxylic acid.

Suitable thioether antioxidants include, but are not limited to, 2-mercaptobenzimidazol; bis-(2-methyl-4-{3-n-alkylthiopropionyloxy}-5-t-butylphenyl)sulfide; dilauryl 3,3'-thiodipropionate; dimyristyl 3,3'-thiodipropionate; distearyl 3,3'-thiodipropionate; ditridecyl 3,3'-thiodipropionate; pentaerythritol-tetrakis-(β-lauryl thiopropionate); and combinations thereof. Suitable thioacetal antioxidants include, but are not limited to, linear and branched dialkyl thioformals and combinations thereof. Suitable boron based antioxidants include, but are not limited to, oil soluble organoborates; alkyl- and aryl-(and mixed alkyl, aryl) substituted borates, and combinations thereof.

Examples of suitable thiocarbamate antioxidants include, but are not limited to, dithiocarbamates such as dialkyl dithiocarbamates, metal thiocarbamates, and combinations thereof. Examples of suitable metal chelating agents include, but are not limited to, alkyl phenols, amines, benzotriazines, EDTA, guanidines, hydroquinones, nucleic acids, pyridines, sulfamides, tetraazaindenes, and combinations thereof.

Suitable copper compounds include, but are not limited to, copper oleates, copper-PIBSA, copper salts, and combinations thereof. Suitable molybdenum compounds include, but are not limited to, oil soluble molybdenum compounds, sulfur containing molybdenum compounds, organomolybdenum compounds and derivatives, and combinations thereof. Examples of some oil soluble molybdenum compounds that may be used in this invention include molybdenum dithioxanthogenates, oxymolybdenum sulfide dithioxanthogenates, molybdenum organophosphorodithioates, oxymolybdenum sulfide organophosphorodithioates, molybdenum carboxylates, molybdenum amine complexes, molybdenum alcohol complexes, molybdenum amide complexes, mixed molybdenum amine/alcohol/amide complexes, and combinations thereof. Various commercially available antioxidant additives may be used in the lubricant layer. Suitable examples include, but are not limited to, phenolic antioxidants such as Irganox® L101 (pentaerythritol tetrakis (3-(3,5-di-tert-butyl-4-hydroxyphenyl)propionate, a high molecular weight phenol), Irganox® L108, Irganox® L130, Irganox® L107 (a high molecular weight phenol), Irganox® L115 (a high molecular weight phenol), Irgafos® 168 (tris-(2,4-di-tert-butylphenyl)phosphite)), Irganox® L109 (a high molecular weight phenol), Irganox® 1010 (tetraester of 3,5-di-tert-butyl-4-hydroxyhydrocinnamic acid with pentaerythritol), Irganox® 1076, Irganox® L1035 (thiodiethylene bis(3,5-di-tert-butyl-4-hydroxyhydrocinnamate)), Irganox® L118 (an ester derivative of a 2,6-di-t-butylphenol), and Irganox® L135 (an ester of 3,5-di-tert-butyl-4-hydroxyhydrocinnamic acid, a high molecular weight phenol), aromatic amine antioxidants such as Irganox® L06 (a phenyl α-naphthyl amine) and Irganox® L57 (an octylated/butylated diphenylamine), blends of hindered phenolic antioxidants and amine antioxidants such as Irganox® L64, Irganox® 74, Irganox® 134, and Irganox® 150, amine antioxidant/antiwear additive blends such as Irganox® L74, and phosphorothionates such as Irgalube® 232 (an ashless butylated triphenyl phosphorothionate) available from Ciba Geigy Specialty Chemicals; hindered phenolic antioxidants such as Vanlube® 691C, aromatic amine antioxidants such as Vanlube® PNA (a phenyl α-naphthyl amine), Vanlube® DND, Vanlube® SL (a diphenylamine), Vanlube® SS (a diphenylamine), Vanlube® 81 (a diphenylamine), and Vanlube® 848 (a diphenylamine), Vanlube® SLHP (a diarylamine), Vanlube® 849 (a diarylamine), Vanlube® NA (a diarylamine), and thiocarbamates such as Vanlube® 7623 (a methylenebis(dialkylthiocarbamate) and Vanlube® 7611 (a methylenebis(dialkylthiocarbamate), and molybdenum compounds such as Molyvan® 855 and Molyvan® 807 available from R. T. Vanderbilt Company, Inc.; aromatic amines such as Additin® M10277, sulfurized olefins such as Additin® RC 2540-A, and sulfurized fatty oils or mixtures of sulfurized fatty oils and olefins such as Additin® R4410, Additin® R4412-F, Additin® R4417, Additin® RC 2515, Additin® RC 2526, Additin® RC 2810-A, Additin® RC 2814-A, and Additin® RC 2818-A available from Rhein Chemie Corporation; aromatic amines such as Lubrizol® 5150A available from The Lubrizol Corporation; amine antioxidants such as Naugalube® 438L (nonylated diphenylamine), Naugalube® AMS (di-α-methylstyryl diphenylamine), Naugalube® 438 (dioctyl diphenylamine), Naugalube® 438R, Naugalube® 640 (butylated/octylated diphenylamine), Naugalube® 680 (octylated/styrenated diphenylamine), Naugalube® 635 (styrenated diphenylamine), Naugalube® TMQ (polymerized trimethylquinoline), Naugalube® 403 (substituted p-phenylenediamine), Naugalube® 410 (substituted p-phenylenediamine), Naugalube® 420 (blend of substituted p-phenylenediamine), Naugard® PANA (phenyl-α-naphthylamine), and Naugalube® 500 (a diarylamine), and phenolic antioxidants Naugard® BHT (di-tert-butyl-p-cresol), and Naugalube® 531 (3,5 di-tert-butyl-4 hydroxy-hydrocinnamic acid, $C_7$–$C_9$ branched alkyl ester) available from Uniroyal Chemical Company, Inc.; amine antioxidants such as Paranox® 14 (a ZDDP) and phenolic antioxidants such as Parabar® 441 (a hindered phenol) available from Exxon Corporation; phenolic antioxidants such as HiTEC® 4701 (a hindered phenol) and sulfurized olefins such as HiTEC' 7084, HiTEC® 7188, HiTEC® 312, and HiTEC® 313 available from Ethyl Petroleum Additives, Inc.; Ethanox 330 (a 1,3,5-trimethyl-2,4,6-tris-(3,5-di-tert-butyl-4-hydroxybenzyl)benzene) available from Ethyl Corporation; phenolic antioxidants such as Sumilizer® BBM-S (4,4'-butylidenebis(2-tert-butyl-5-methylphenol)), Sumilizer® WX-R (4,4'-thiobis(2-tert-butyl-5-methylphenol)), Sumilizer® NW (alkylated bisphenol), Sumilizer® BHT (2,6-di-t-butyl-4-methylphenol), Sumilizer® MDP-S (2,2'-methylenebis(6-tert-butyl-4-methylphenol)), Sumilizer® GM (2-tert-butyl-6-(3-tert-butyl-2-hydroxy-5-methylbenzyl)-4-methylphenylacrylate), Sumilizer® GS (2-[1-(2-hydroxy-3,5-di-tert-pentylphenyl)ethyl]-4,6-di-tert-pentylphenylacrylate), Sumilizer® BP-76 (octadecyl 3-(3, 5-di-tert-butyl-4-hydoroxyphenol)propionate), Sumilizer® S, Sumilizer® BP-101 (pentaerythrityltetrakis [3-(5-di-tert-butyl-4-hydoroxyphenol)-propinate]), and Sumilizer® GA-80 (3,9-bis[3-3-tert-butyl-4-hydroxy-5-methylphenyl)-propionyloxy]-1,1-dimethylethyl]-2,4,8,10-tetraoxaspiro-[5.5]undecane), and phosphite antioxidants Sumilizer® TNP, Sumilizer® TPP-R, and Sumilizer® P-16 (tris(2,4-ditert-butylphenyl)-phosphite), and thioether antioxidants such as Sumilizer® TPL-R (dialuryl 3,3'-thiodipropionate), Sumilizer® TPM (dimyristyl 3,3'-thiodiprodionate), Sumilizer® TPS (distearyl 3,3'-thiodiprodionate), Sumilizer® TP-D (pentaerythrityltetrakis-(3-dodecylthiopropionate)), Sumilizer® TL, and Sumilizer® MB available from Sumitomo Chemical Co. Ltd.; phosphite antioxidants Adekastab PEP-2, Adekastab PEP-4C, Adekastab PEP-8, Adekastab PEP-8F, Adekastab PEP-8W, Adekastab PEP-11C, Adekastab PEP-24G, Adekastab PEP-36, Adekastab HP-10, Adekastab 2112, Adekastab 260, Adekastab P, Adekastab QL, Adekastab 522A, Adekastab 329K, Adekastab 1178, Adekastab 1500, Adekastab C, Adekastab 135A, Adekastab 517, Adekastab 3010, and Adekastab TPP and phenol antioxidants Adekastab AO-20, Adekastab AO-30, Adekastab AO-40, Adekastab AO-50 (n-octadecyl-3-(3,5-di-t-butyl-4-hydroxyphenyl)propionate), Adekastab AO-60 (tetrakis-{methylene-3-(3,5-di-t-butyl-4-hydroxyphenyl)propionate}methane), Adekastab AO-75, Adekastab AO-80 (3,9-bis-[2-{3-(3-t-butyl-4-hydroxy-5-methylphenyl)propionyloxy}-1,1-dimethylethyl]-2,4,8,10-tetraoxaspiro{5,5}undecane), Adekastab AO-330, Adekastab AO-616, Adekastab AO-635, Adekastab AO-658, Adekastab AO-15, Adekastab AO-18, Adekastab 328, and Adekastab AO-37, thioether antioxidants such as Adekastab AO-23, Adekastab AO-412S, and Adekastab AO-503A and molybdenum compounds such as Sakura-Lube° 100 (molybdenum dithiocarbamate), Sakura-Lube° 155, Sakura-Lube® 600, and Sakura-Lube® 700 available from Asahi Denka Kogyo K. K.; phenol antioxidants such as Sanol LS 2626 (1-[2-{3-(3,5-di-t-butyl-4-hydroxyphenyl)propionyloxy}ethyl]-4-{3-(3,5-di-t-butyl-4-hydroxyphenyl)propionyloxy}-2,2,6,6-tetramethylpiperidine) available from Sankyo K. K.; diarylamines such as Goodrite® 3123, Goodrite® 3190X36, Goodrite® 3127, Goodrite® 3128, Goodrite® 3185X1, Goodrite® 3190X29, Goodrite® 3190X40, and Goodrite® 3191 available from BF Goodrich Specialty Chemicals; oil soluble molybdenum compounds such as molybdenum octoate available from The Shepherd Chemical Company; and molybdenum HEX-CEM available from The OM Group.

While the antioxidants listed above are particularly useful in embodiments of the invention, the foregoing description is not intended to limit other available antioxidants. It will be appreciated that other antioxidants can likewise be employed in the practice of this invention either alone or in combination with other selected ingredients or coadditives.

As discussed above, antiwear agent additives including ashless antiwear agent additives may also be used in combination with the cyclopentanes, cyclopentenes, and cyclopentadienes in forming a lubricant layer. Antiwear agents, as their name implies, reduce wear which occurs when two metal surfaces rub together. The antiwear agents which may be employed in the lubricant composition are not particularly limited and may be any conventional antiwear agent known to those skilled in the art. Suitable antiwear agents for use in embodiments of the invention are generally polar molecules which exhibit strong adhesion to the metal surface and a nonpolar chain that will orient itself perpendicularly to the surface to create a film. Representative of conventional antiwear agents which may be used include, for example, zinc dialkyl dithiophosphates and zinc diaryl dithiophosphates.

Suitable antiwear agents include, but are not limited to, amine derivatives of dithiophosphoric acid compounds; amine phosphates; amine salts of mono- or dialkylphosphoric acids, mono- or dihexylphosphates, alkylphosphonic acids such as amine salts of methylphosphonic acids; benzotriazoles such as bis(2-ethylhexyl)aminomethyltolutriazole; bisdithiocarbamate esters; boron-containing compounds such as borates and borate esters; cyclic phosphates; derivatives of 2,5-dimercapto-1,3,4-thiadiazole such as 2,5-bis(tert-nonylditdithio)-1,3,4-thiadiazole; derivatives of 2-mercaptobenzothiazole such as 1-[N,N-bis(2-ethylhexyl)aminomethyl]-2-mercapto-1H-1,3-benzothiazole; dialkyl dithiocarbamate-derived organic ethers; dialkyl phosphites such as dioctyl phosphite; dihydrocarbyl dithiophosphates such as metal salts of dihydrocarbyl dithiophosphoric acid; dithiocarbamates; dithiocarbamic acids; dixanthogens such as diethoxyethyl dixanthogen; ethoxylated amine dialkyldithiophosphates and ethoxylated amine dithiobenzoates; fatty acids such as palmitic and stearic acids and their esters; hydroxy-substituted aromatic groups; isopropyl phenylphosphates; mercaptothiadiazoles; metal alkoxyalkylxanthates such as nickel ethoxyethylxanthate; metal alkylaryldithiophosphates such as zinc alkylaryldithiophosphates; metal alkyldithiophosphates; metal carbamates; metal dialkyldithiophosphates such as zinc dialkyldithiophosphate and zinc-bis(2-ethylhexyl)dithiophosphate; metal diaryldithiophosphates such as zinc diaryldithiophosphates; metal dithiophosphates such as zinc dithiophosphate and zinc dihydrocarbyl dithiophosphate; metal phosphates; metal phosphorodithioates; metal thiocarbamates and dithiocarbamates such as methylene-bis-dibutyidithiocarbamate; zinc dithiocarbamates; zinc diamyldithiocarbamates; molybdenum dithiocarbamates; metal thiophosphates such as zinc dithiophosphates; metallic salts of fatty acids and naphthenic acids; molybdenum carboxylates; molybdenum phosphorodithioates; molybdenum dithiocarbamates; molybdenum xanthates; oleic acids; organic sulfur-containing compounds; organo borates; organo phosphites; organo thioalkyl borates; organomolybdenum complexes including oil soluble or oil dispersible phosphorus-free organomolybdenum compounds; phenols such as hindered phenols; phosphate ester amines; phosphate esters; phosphite ester amines; phosphite esters; phosphorodithioate compositions such as phosphorodithioate esters; phosphorodithioic acids; phosphorothiolothionates; phosphosulfurized hydrocarbons; substituted trialkyl mono- or dithiophosphates such as [(diisopropoxyphosphinothioyl)thio]propionate and butylene-1,3-bis[(diisobutoxyphosphinothioyl)propionate]; sulfur- and/or phosphorus- and/or halogen-containing compounds such as chlorinated paraffins; sulfurized olefins or vegetable oils such as soybean oils and rapeseed oils; alkyl- or aryl-di- or -trisulfides; sulfur compounds; sulfurized olefins; triaryl monothiophosphates such as triphenyl thionophosphates, tris-[isononylphenyl]thionophosphates, and tert-butylated triphenyl thionophosphates; triaryl phosphites such as tris[nonylphenyl]phosphite); triarylphosphates such as tritolylphosphate; tricresyl phosphates; trithiophosphates such as trithiophosphoric acids; and S,S,S-tris(isooctyl-2-acetate); vegetable oils and fats; and combinations thereof.

Examples of ashless antiwear additives include, but are not limited to, dithiophosphate esters; dithiophosphoric acid esters; ethylene-propylene diene modified copolymers and their derivatives; thiadiazole derivatives such as a 2-mercapto-1,3,4-thiadiazole derivative; alkylated or alkarylated dithiocarbamates; zinc dialkyldithiophosphates; sulfur-containing organo-phosphorus compounds; ethoxylated amine dialkyldithiophosphates and dithiobenzoates; dithiophosphates such as triphenylphosphorothionates; imidazole thiones; derivatives of substituted linear thioureas such as N-acyl-thiourethane thioureas; and combinations thereof.

Various commercially available antiwear agents may be used. Suitable examples include, but are not limited to, Vanlube® 7723 and Vanlube® 732 available from R. T. Vanderbilt Company, Inc. and Irgalube'211, Irgalube®232, Irgalube® 349, Irgalube® DDPP, and Irganox® F10 available from Ciba Geigy Specialty Chemicals.

While the antiwear agents listed above are particularly useful in embodiments of the invention, the foregoing description is not intended to limit other available antiwear agents. It will be appreciated that other antiwear agents can likewise be employed in the practice of this invention either alone or in combination with other selected ingredients or coadditives.

As discussed above, friction modifier additives may also be used in combination with the cyclopentanes, cyclopentenes, and cyclopentadienes in forming a lubricant layer. Friction modifier additives, as their name implies, impart friction characteristics to lubricants. Suitable friction modifier additives include, but are not limited to, 1-hydroxyalkyl-2 alkyl imidazolines such as 1-hydroxyethyl-2-heptacecyl-2-imidazoline; 2,2'-di-(n-dodecylthio)-diethyl ethers; aliphatic carboxylic acids; aliphatic carboxylic esters; alkane phosphonic acid salts; alkylene oxide adducts of phosphosulfurized -(hydroxyalkyl) alkenyl succinimides; amides such as aliphatic fatty acid amides, aliphatic carboxylic ester amides, fatty acid amides; amines such as aliphatic amines, aromatic amines, ethoxylated aliphatic amines, alkoxylated fatty amines, hydroxy ether amines, hydroxyl amines such as polyoxyethylene tallow amine, hydroxy amines, oxyalkylated aliphatic tertiary amines, ether amines, phosphate ester amines, oil-soluble alkoxylated mono- and diamines, fatty amines such as N-fatty diethanolamines, polyalkenyl substituted succinimides of alkylene polyamines; boron containing compounds such as borated alkoxylated fatty amines, borated glycerol esters, borated glycerol monocarboxylates, borated fatty epoxides, organoborates, phenolic borates; dithiocarbamate lubricants such as those derived from a secondary amine, carbon disulfide, an allyl halide, and a 2-dimercapto-1,3,4-thiadiazole; esters such as glycerol esters, glycol esters, polyalcohol (partial) esters, sorbitan esters, phosphate esters, phosphite esters, hydrocarbyl substituted succinate esters of thiobisethanol, metal ester salts of succinate esters, esters formed by reacting carboxylic acids and anhydrides with alkanols, compounds having polar terminal groups such as carboxyl or hydroxyl groups covalently bonded to an oleophillic hydrocarbon chain; succinate esters or metal salts thereof; fatty acid esters and amides; glycerol esters of dimerized fatty acids; glycerol mono and dioleates; higher alcohols; ISA-TEPA; molybdenum complexes of poly-isobutenyl succinic anhydride-amino alkanols; N-(hydroxyalkyl) alkenylsuccinamic acids or succinimides; n-dodecyl-(2-hydroyethyl) sulfides; octadecenyl succinic acids; oils and fats such as fatty acids, fatty epoxides, fatty phosphites, glycerol esters of dimerized fatty acids, metal salts of fatty acids, fatty acid esters, fatty imidazolines; oil-soluble molybdenum compounds, organomolybdenum compounds and derivatives, molybdenum compounds such as dialkyldithiocarbamates, molybdenum dialkyl dithiophosphates, molybdenum complexes of polyisobutenyl succinic anhydride-amino alkanols; phosphates such as aliphatic phosphates, aliphatic thiophosphonates, aliphatic thiophosphates; reaction products of phosphonates with oleamides; reaction products of di-(lower alkyl) phosphites and epoxides; S-carboxy-alkylene hydrocarbyl succinimide; S-carboxy alkylene hydrocarbyl succinamic acid; succinate esters or metal salts of hydrocarbyl substituted succinic acids or anhydrides; thiobis alkanol amides; sulfurized compounds such as sulfurized olefins, sulfurized fatty acid esters, sulfurized esters; alkylene oxide adducts of phosphosulfurized -(hydroxyalkyl) alkenyl succinimides; thioether hydroxyamines; zinc oleates, and combinations thereof.

Various commercially available friction modifier additives may also be used. Suitable examples include, but are not limited to, hydroxyl amine compounds such as Ethomeen®, Ethomeen® T/12 (polyoxyethylene tallow amine), Ethomeen® C/15, Ethoduomeen® T/12, Ethoduomeen® T/15 available from Armak Chemical Division of Akzo Chemie.

While the friction modifiers listed above are particularly useful in embodiments of the invention, the foregoing description is not intended to limit other available friction modifiers. It will be appreciated that other friction modifiers can likewise be employed in the practice of this invention either alone or in combination with other selected ingredients or coadditives.

The amount of additive(s) for use in the lubricant layer depends on a variety of factors such as customer requirements and applications, the desired level of antioxidant protection required, the desired level of antiwear performance required, and the desired level of friction modification required. The amount of additive incorporated into the lubricant composition should be an amount which provides effective durability and performance. In some embodiments, the amount of additive(s) present in the lubricant layer may range from about 0.1 wt. % to about 20 wt. % based on the total weight of the lubricant composition. In certain other embodiments, the amount of additive(s) present in the lubricant layer may range from about 0.1 wt. % to about 10 wt. % based on the total weight of the lubricant composition. In still other embodiments, the amount of the additive present in the lubricant layer may range from about 2 wt. % to about 5 wt. % based on the total weight of the lubricant composition.

While the additives listed above are particularly useful in embodiments of the invention, the foregoing description is not intended to limit other available additives. It will be appreciated that other additives can likewise be employed in the practice of this invention either alone or in combination with other coadditives. Additional useful additives are disclosed in the following U.S. patents, the disclosures of which are herein incorporated by reference in their entirety: U.S. Pat. Nos. 3,451,166; 3,458,495; 3,470,099; 3,511,780; 3,687,848; 3,770,854; 3,778,375; 3,779,928; 3,850,822; 3,852,205; 3,876,733; 3,879,306; 3,929,654; 3,932,290; 3,933,659; 4,028,258; 4,105,571; 4,115,287; 4,136,041; 4,153,562; 4,176,074; 4,344,853; 4,367,152; 4,737,301; 5,078,893; 5,498,809; and 5,840,672.

Various methods are known in the art for forming a lubricant layer over a magnetic layer. For example, a lubricant film may be formed by coating or spraying a solution of a lubricant in an organic solvent onto a substrate (e.g., a non-magnetic support having thereon a magnetic film) and letting the solvent evaporate. Another method includes rubbing a substrate having a magnetic layer with an object impregnated with a lubricant to transfer the lubricant thereto. Still another method includes immersing a substrate with a magnetic layer in a solution of a lubricant in an organic solution to let the lubricant be adsorbed onto the substrate. Furthermore, the lubricant layer may be formed by the method referred to as the "Langmuir-Blodgett" method. The Langmuir-Blodgett method may be used to construct a monomolecular or multimolecular layer in a film. This method is described generally in U.S. Pat. No. 4,907,038. The lubricant layer may also be formed by a vapor deposition technique.

In some embodiments, a lubricant layer is formed by dip-coating, coil-bar coating, or gravure coating followed by drying. A variety of solvents may be used in this method, such as ethanol, methanol, benzene, toluene, acetone, cyclohexane, heptane, ethyl ether, dichloromethane, isopropanol, petroleum naphtha, ethyl acetate, methyl ethyl ketone, and so on. Although CFCs and related solvents also may be used, they are not preferred due to their adverse environmental effects.

The following examples are given to illustrate embodiments of the invention and are not intended to limit the scope of the invention as otherwise described. All numbers disclosed herein are approximate values.

EXAMPLE 1

This example demonstrates that Pennzane® X-2000, a lubricant made of tris-(2-octyldodecyl)cyclopentane, has a lower friction coefficient and comparable wear resistance to Z-DOL®, an existing lubricant. Pennzane°X-2000 is a product available from Pennzoil-Quaker State, Inc., Houston, Tex. Z-DOL® is a functionalized PFPE manufactured by Ausimont Montedison.

For comparison, Pennzane® X-2000 and Z-DOL® samples were tested for wear scar. Their friction coefficients also were measured. The tests were conducted in accordance with ASTM D5707-95 and DIN 51 834 methods. A description of the ASTM D5707-95 and DIN 51 834 methods can be found in the article entitled: *New ASTM and DIN Methods for Measuring Tribological Properties Using the SRV® Test Instrument*, printed in *NLGI Spokesman*, Vol.60, No. 12, page 17 (March 1997). This article is incorporated by reference in its entirety herein.

The test results are summarized in Table I. A number of additives were used with Pennzane® X-2000 and Z-DOL®. They included: tricresyl phosphate; oleic acid; Irgalube® 63; Irgalube® 232; glycerol monooleate; and Sakura-Lube® 100. Irgalube® 63 is an ashless dithiophosphate available from Ciba Geigy Specialty Chemicals; Irgalube® 232 is an ashless butylated triphenyl phosphorothionate available from Ciba Geigy Speciality Chemicals; and Sakura-Lube® 100 is a molybdenum dithiocarbamate available from Asahi Denka Kogyo K. K.

It can be seen from Table 1 that the friction coefficients of Pennzane® X-2000 with various additives generally are lower than those of Z-DOL® with the same additives. The wear resistance of Pennzane® X-2000 generally is comparable to or better than that of Z-DOL®.

EXAMPLE 2

This example demonstrates that Pennzane® X-2000 lubricant films formed on a magnetic medium have a longer lifetime in contact-start/stop cycles than Z-DOL® lubricant films.

A number of samples that included a magnetic medium with a lubricant film formed thereon were prepared. Lubricant films of both Pennzane® X-2000 and Z-DOL® were deposited on amorphous hydrogenated carbon overcoated disks. The lubricant films were formed by dipping the magnetic medium disks into a solution containing the respective compositions at a specified weight percentage. 1,1,2-trichloro-trifluoroethane was used as the solvent for Z-DOL®, whereas cyclohexane was used as the solvent for Pennzane® X-2000. These samples were tested in an apparatus called a High-Velocity Ball-on-Inclined-Plane ("HVBOIP") tester, which generates tribological conditions similar to the magnetic head/disk interface in a computer disk drive.

Figure 3:
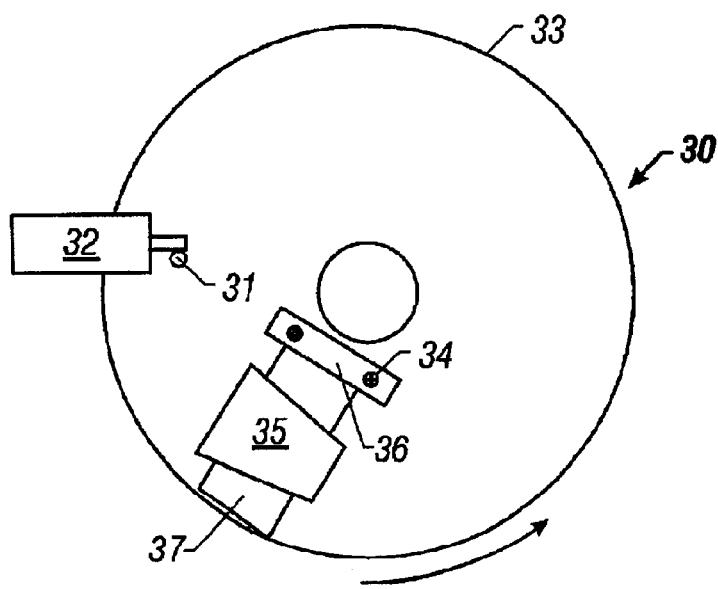
FIG. 3 is a schematic showing the top view of the High Velocity Ball-on-Inclined Plane tester used in an embodiment of the intention.

FIG. 3 shows schematically the top view of the HVBOIP tester 30. Referring to FIG. 3, a ruby ball 31 with a radius of about 1.59 mm is held at one end of a strain gauge 32. The ruby ball is polished by using a diamond paste of 1 micron average particle diameter and has a surface roughness, $R_a$ of about 2.1 nm and a $R_{max}$ of about 19.4 nm. The strain gauge 32 has a force resolution of about 0.1 mN. The test sample is cut from a super-smooth disk (with about 75 Å thick hydrogenated carbon overcoat) and is mounted on another disk. A disk section 35 is glued to a substrate 37, and a substrate clamp 36 is held down by a pair of screws 34.

A spin stand (not shown) is used to rotate the disk. The sample is mounted on the disk using successive applications of a dilute glue solution in a staircase form. The glue controls the angle of inclination. In this way, a 0.001° inclination angle can be achieved. When the test commences, the disk is rotated at a speed of about 2 m/s, and the ball is stationary. For every revolution, the ball slides on the incline plane once at the angle the glue controls. This simulates impact, landing, and take off. Because the angle of inclination increases the test severity, the total number of cycles required to reach failure can be shortened. The test is conducted in a class 10 clean room.

TABLE I

| Additives | Friction Coefficient | | | | Wear Scar (mm) | |
| --- | --- | --- | --- | --- | --- | --- |
| | 15 min. | | 120 min. | | | |
| | Pennzane ® X-2000 | Z-DOL ® | Pennzane ® X-2000 | Z-DOL ® | Pennzane ® X-2000 | Z-DOL ® |
| Tricresyl Phosphate | 0.096 | 0.125 | 0.108 | 0.122 | 0.56 × 0.59 | 0.61 × 0.68 |
| Oleic acid | 0.114 | 0.112 | 0.142 | 0.100 | 0.90 × 1.01 | 0.86 × 0.89 |
| Ashless dithiophosphate | 0.097 | 0.128 | 0.083 | 0.117 | 0.73 × 0.75 | 0.63 × 0.66 |
| Ashless butylated triphenyl phosphorothionate | 0.101 | 0.127 | 0.094 | 0.130 | 0.51 × 0.49 | 0.92 × 0.95 |
| Glycerol monooleate | 0.118 | 0.116 | 0.099 | 0.113 | 0.86 × 0.86 | 0.87 × 0.92 |
| Molybdenum dithiocarbamate | 0.135 | 0.110 | 0.132 | 0.106 | 0.80 × 0.88 | 0.77 × 0.83 |

The test procedure is divided into two steps. In the first step, the disk is accelerated to the test speed of about 2 m/s (760 rpm) at about 0.1 second and rotated at the test speed for 100 sliding cycles, and then the test was stopped. The acceleration or deceleration step to the desired speed is accomplished within one rotational cycle, so that the effect on test speed throughout the test is negligible. These 100 cycles constitute a unit test cycle. Because of the high test speed, the data acquisition rate for the test apparatus of 5000 inputs per second is inadequate. Only few data points on the frictional force could be collected.

To correct for this inadequacy, after every 100 high speed test cycles, the second step of the test procedure is applied to examine the surface damage as well as to measure accurately the frictional force. In the second step, the sample is rotated at a very slow speed of about 0.05 m/s (2 rpm). This allows the measurement of the frictional force between the ball and the inclined plane sample and also allows direct observation of the sample surface via a video camera. These two steps are repeated for each unit cycle until the sample failed. The failure of the sample is indicated by a sudden drastic increase in frictional force. The entire test procedure is controlled by a computer.

Figure 4:
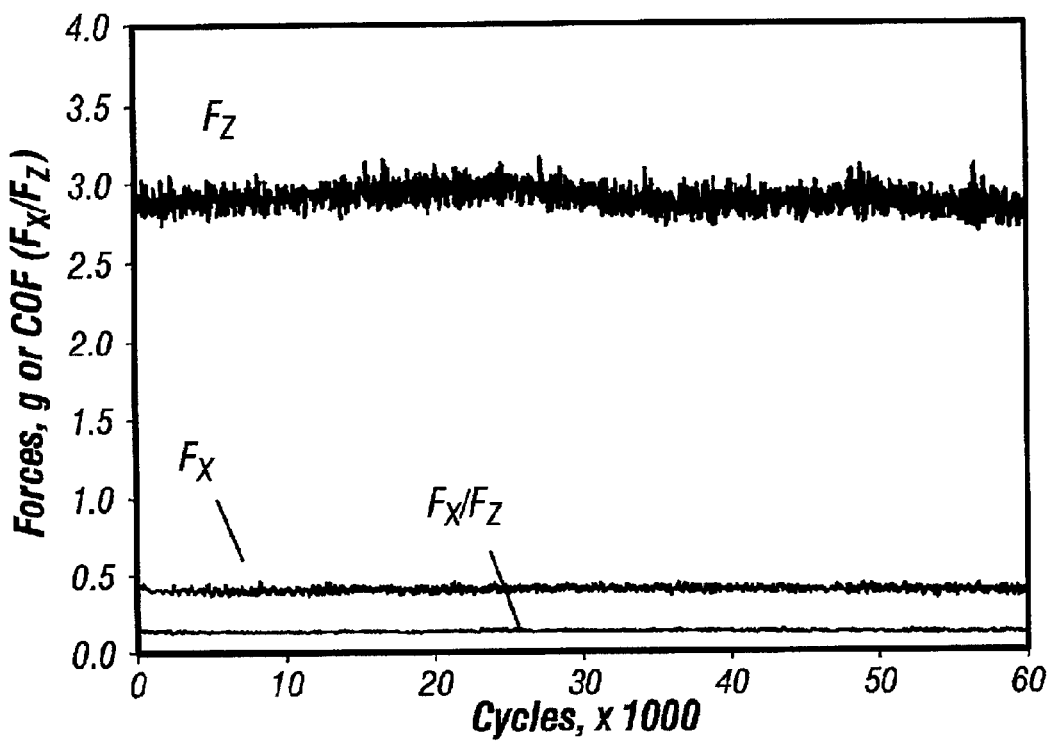
FIG. 4 is a plot of coefficient of friction as a function of number of cycles for Pennzane® Synthesized Hydrocarbon Fluid X-2000.
Figure 5:
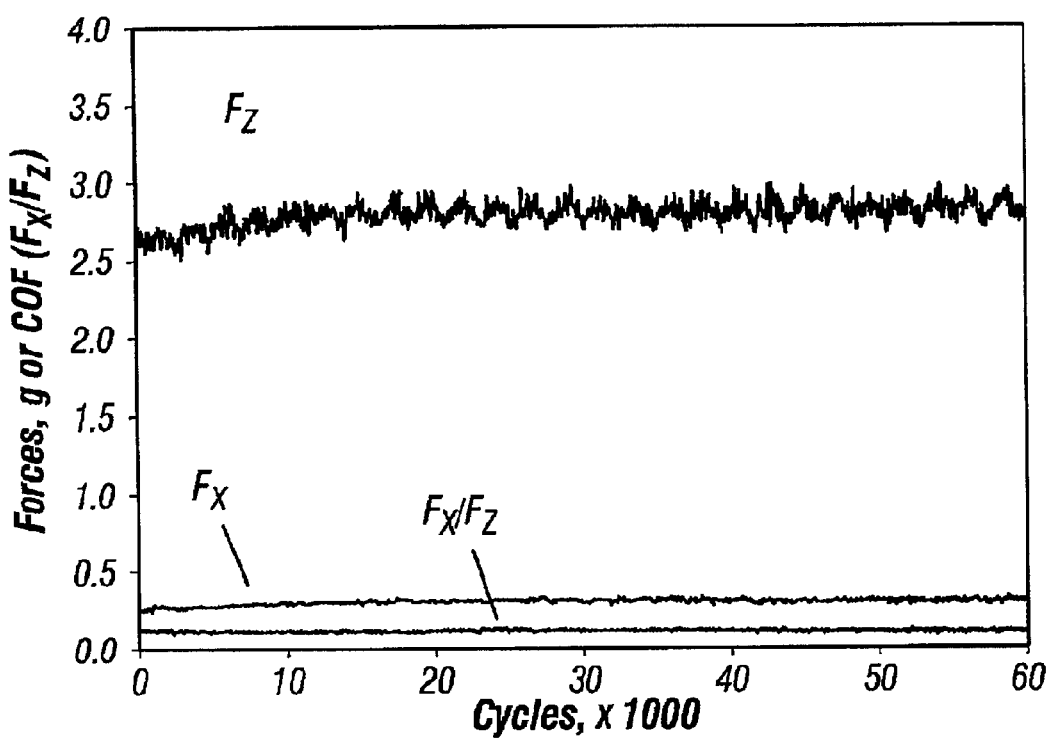
FIG. 5 is a plot of coefficient of friction as a function of number of cycles for Pennzane® Synthesized Hydrocarbon Fluid X-2000.

Four lubricant films (Sample Nos. 1–4) were made from a solution containing Pennzane® X-2000 at 0.055 wt. % (Sample No. 1), 0.11 wt. % (Sample No. 2) and 0.22 wt. % (Sample No. 3) and Z-DOL® at 0.1 wt. % (Sample No.4), respectively. These films were tested in the HVBOIP tester. Both normal force $F_z$ and frictional force $F_x$ for each film were measured. The coefficient of friction is the ratio of $F_x/F_z$. FIGS. 4 and 5 are plots for two Pennzane® X-2000 lubricant films. In both figures, normal force $F_z$, frictional force $F_x$, and coefficient of friction $F_x/F_z$ are plotted as a function of the number of cycles. The coefficient of friction for the Pennzane® X-2000 lubricant film with 0.11 wt. % is about 0.4, whereas the coefficient of friction for the Pennzane® X-2000 lubricant films with 0.22 wt. % is decreased to about 0.25.

Figure 6:
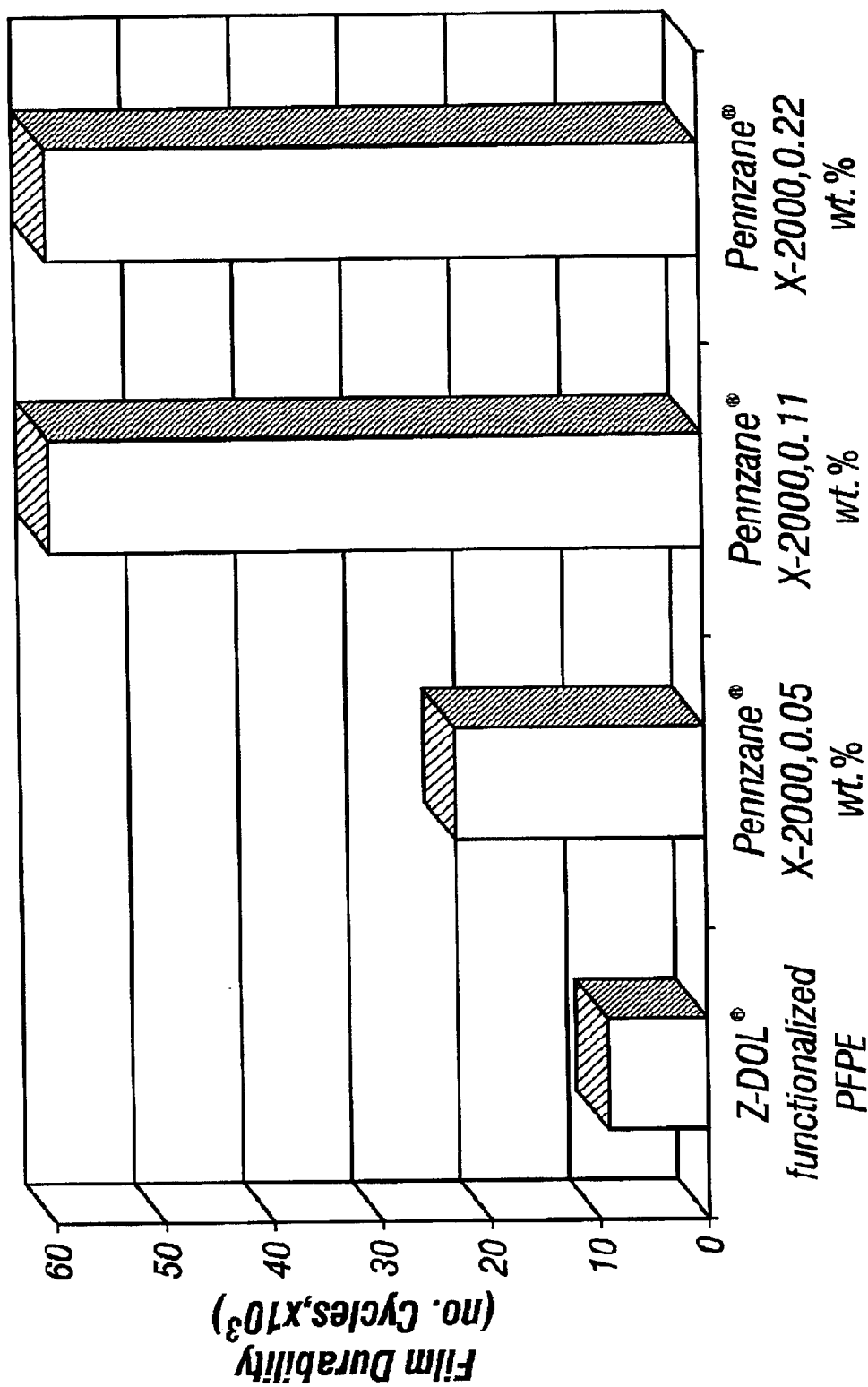
FIG. 6 is a plot which compares the film durability of various lubricants.

In addition to the coefficient of friction, the number of cycles to failure was also measured, and the data are present in Table II and FIG. 6. It is notable that the Pennzane® X-2000 lubricant films lasted longer than the Z-DOL® lubricant film. The films made from a solution containing 0.11 wt. % and 0.22 wt. % of Pennzane® X-2000 are at least six times more durable than the Z-DOL® lubricant film. Therefore, disk drives incorporating Pennzane® X-2000 or similar lubricants should have longer lifetime and improved performance.

TABLE II

| Sample Nos. | Lubricant | Number of Cycles to Failure |
|---|---|---|
| 1 | Z-DOL ® (0.1 wt. %) | 8,000 to 10,000 |
| 2 | Pennzane ® X-2000 (0.055 wt. %) | 10,000 to 35,000 |
| 3 | Pennzane ® X-2000 (0.11 wt. %) | greater than 60,000 |
| 4 | Pennzane ® X-2000 (0.22 wt. %) | greater than 60,000 |

EXAMPLE 3

This example demonstrates that Pennzane® X-2000 lubricant films which contain one or more additives formed on a magnetic medium have a longer lifetime in contact-start/stop cycles than Z-DOL® lubricant films.

Four samples (Sample Nos. 5–8) that included a magnetic medium with a lubricant film formed thereon were prepared. One sample (Sample No. 5) included a magnetic medium with a Z-DOL® lubricant film formed thereon. Three samples (Samples Nos. 6–8) included a magnetic medium with a Pennzane® X-2000 lubricant film formed thereon which contained one or more additives. The lubricant films were deposited on amorphous hydrogenated carbon overcoated disks using the dip procedure described in Example 2. The four lubricant films were formed by dipping the magnetic medium disks into a solution containing the respective compositions at a specified weight percentage. 1,1,2-trichloro-trifluoroethane was used as solvent for Z-DOL®, whereas cyclohexane was used as solvent for Pennzane® X-2000 containing the additive(s).

Sample No. 5 was a lubricant film made from a solution containing Z-DOL® at 0.1 wt. %. Sample No. 6 was a lubricant film made from a solution containing Pennzane® X-2000 and Irganox® L109 in a ratio of 95:5 by weight. Irganox® L109 is a hindered phenolic antioxidant available from Ciba Geigy Specialty Chemicals. Sample No.7 was a lubricant film made from a solution containing Pennzane® X-2000, Irganox® L109, and Dow® X-1P in a ratio of 90:5:5 by weight. Dow® X-1P is a phosphazine available from Dow. Sample No. 8 was a lubricant film made from a solution containing Pennzane® X-2000, Irganox® L109, and tricresyl phosphate in a ratio of 90:5:5 by weight.

Figure 7:
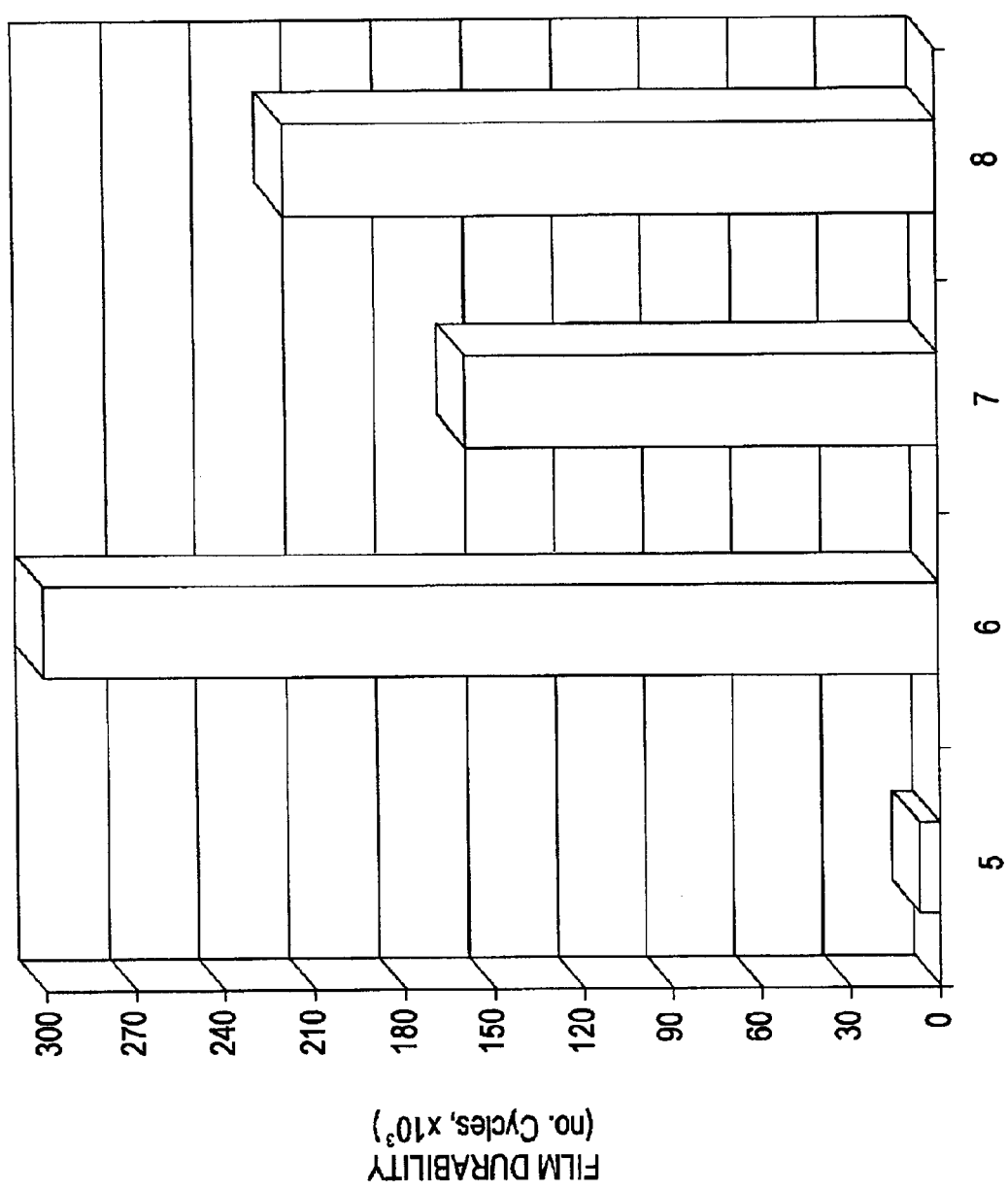
FIG. 7 is a plot which compares the film durability of various lubricants.

In addition to the coefficient of friction, the number of cycles to failure was also measured, and the data are present in Table III and FIG. 7.

TABLE III

| Sample Nos. | Lubricant | Number of Cycles to Failure |
|---|---|---|
| 5 | Z-DOL ® | 8,000 to 10,000 |
| 6 | Pennzane ® X-2000 containing a hindered phenolic antioxidant | greater than 300,000 |
| 7 | Pennzane ® X-2000 containing a hindered phenolic antioxidant and phosphazine | greater than 160,000 |
| 8 | Pennzane ® X-2000 containing a hindered phenolic antioxidant and tricresyl phospate | greater than 220,000 |

It is notable that the Pennzane® X-2000 lubricant films containing additives lasted longer than the Z-DOL® lubricant film. In particular, the films made from a solution containing Pennzane® X-2000 and the hindered phenol antioxidant in a ratio of 95:5 by weight were at least thirty times more durable than the Z-DOL® lubricant film. Therefore, disk drives incorporating Pennzane® X-2000 containing additives (and hindered phenolic antioxidants in particular) or similar lubricants should have longer lifetime and improved performance.

EXAMPLE 4

This example demonstrates that fluorinated Pennzane® X-2000 compounds are compatible with a range of hydrocarbons. The solubility of four fluorinated Pennzane® X-2000 samples (Sample Nos. 9–12) was tested in three solvents: (1) cyclohexane; (2) fluorobutene methoxy ether; and (3) 1,1,2-trifluorethane.

Sample No. 9 was a compound having the following formula:

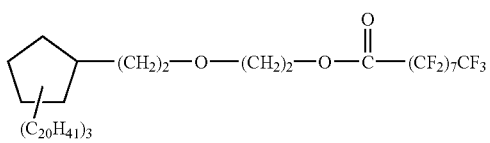

Sample No. 10 was a compound having the following formula:

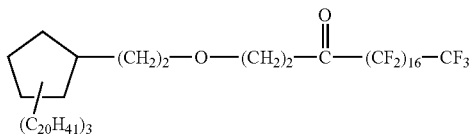

Sample No. 11 was a compound having the following formula:

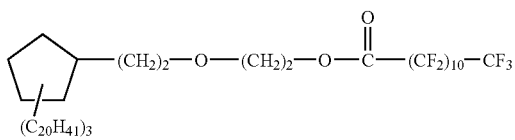

Sample No, 12 was a compound having the following formula:

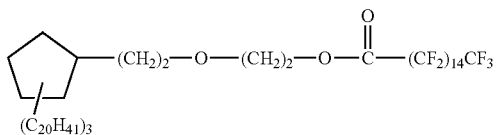

The solubility of Sample No. 12 was tested two times (shown as Sample Nos. 12a and 12b below). The solubility test results are shown in Table IV:

TABLE IV

| | Solvent | | |
|---|---|---|---|
| Sample No. | Cyclohexane | Flourobutene Methoxy ether | 1,1,2-trifluorethane |
| 9 | Yes | Not Tested | Not Tested |
| 10 | Yes | Not Tested | Not Tested |
| 11 | Yes | No | Yes |
| 12a | Yes | No | Yes |
| 12b | Yes | Not Tested | Note Tested |

The miscibility of Sample Nos. 5–8 in a Pennzane® X-2000 solution at various weight percents was also tested. The test results are shown in Table V:

TABLE V

| | Pennzane ® X-2000 Solution | | | |
|---|---|---|---|---|
| Sample No. | 1 wt. % | 5 wt. % | 5 wt. % | 10 wt. % |
| 9 | Yes | Yes | Yes | No |
| 10 | Yes | Yes | Yes | No |
| 11 | Yes | Yes | Yes | Not Tested |

TABLE V-continued

| | Pennzane ® X-2000 Solution | | | |
|---|---|---|---|---|
| Sample No. | 1 wt. % | 5 wt. % | 5 wt. % | 10 wt. % |
| 12a | Yes | Yes | Not Tested | Not Tested |
| 12b | Yes | Yes | Yes | No |

This example demonstrates that fluorinated Pennzane® X-2000 compounds are soluble in hydrocarbon solvents and miscible in Pennzane® X-2000, a lubricant made of tris-(2-octyldodecyl)cyclopentane, up to 10 wt. %.

EXAMPLE 5

This example demonstrates the number of cycles to failure of lubricant films containing Pennzane® X-2000, derivatives of Pennzane® X-2000, and Pennzane® X-2000 compounds containing an additive as a function of the thickness of the film.

Four samples (Sample Nos. 13–16) that included a magnetic medium with a lubricant film formed thereon were prepared. The lubricant films were deposited on amorphous hydrogenated carbon overcoated disks using the dip procedure described in Example 2. The four lubricant films were formed by dipping the magnetic medium into a solution containing the respective compositions at a specified weight percentage. Cyclohexane was used as the solvent for Sample Nos. 13–16.

Sample No. 13 was a lubricant film made from a solution containing Pennzane® X-2000 at 0.055 wt. % having a thickness of 14.5 Å. Sample No. 14 was a lubricant film made from a solution containing Pennzane® D-600 at 0.055 wt. % having a thickness of 5.2 Å. Pennzane® D-600 is a trialkyl cyclopentane available from Pennzoil-Quaker State, Inc., Houston, Tex. having an average molecular weight of 446. Sample No. 15 was a lubricant film made from a solution containing a Pennzane® dimer amine represented by the following formula:

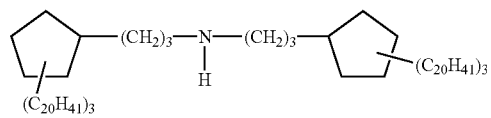

at 0.055 wt. % having a thickness of 32.6 Å. Sample No. 16 was a lubricant film made from a solution containing Pennzane® X-2000 and Irganox® L 109 in a ratio of 95:5 by weight having a thickness of 11.1 Å.

Figure 8:
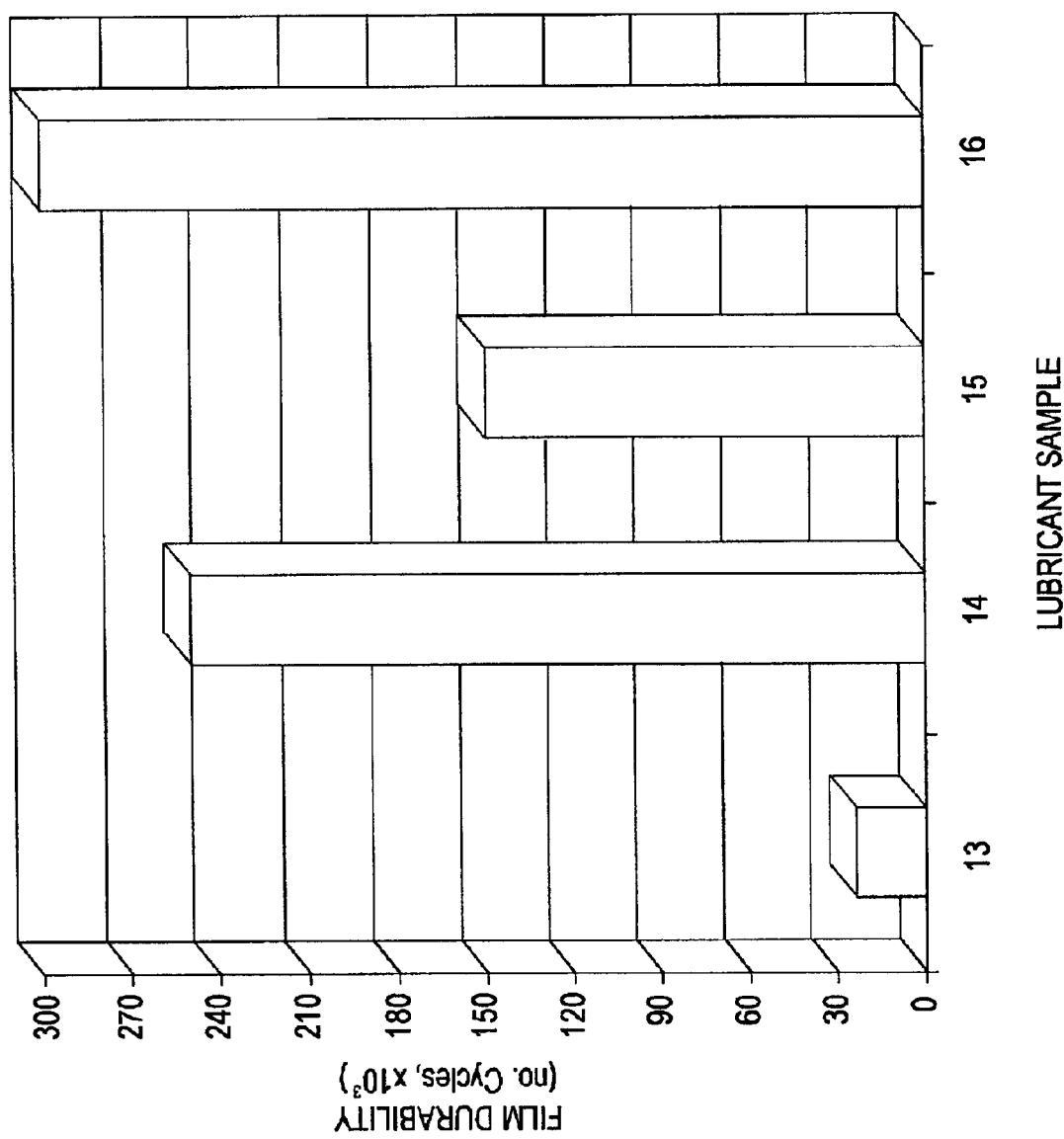
FIG. 8 is a plot which compares the film durability of various lubricants.

Sample Nos. 13–16 were tested in the HVBOIP tester using the test procedures described in Example 2 above. The number of cycles to failure was also measured, and the data are present in Table VI and FIG. 8.

TABLE VI

| Sample No. | Lubricant | Film Thickness (Å) | Number of Cycles to Failure |
|---|---|---|---|
| 13 | Pennzane ® X-2000 | 14.5 | 10,000 to 35,000 |
| 14 | Pennzane ® D-600 | 5.2 | 250,000 |
| 15 | Pennzane ® dimer amine | 32.6 | 150,000 |
| 16 | Pennzane ® X-2000 containing a hindered phenolic antioxidant | 11.1 | greater than 300,000 |

It is notable that the film containing the Pennzane® X-2000 containing the hindered phenolic antioxidant additive was at least eight times more durable than the Pennzane® X-2000 compound. It is also notable that the film containing the low molcular weight Pennzane® D-600 sample was at least seven times more durable than the Pennzane® X-2000 compound. Therefore, disk drives incorporating hindered phenolic antioxidants in Pennzane® fluids should have longer lifetime and improved performance.

EXAMPLE 6

This example demonstrates the number of cycles to failure of lubricant films containing Pennzane® X-2000, derivatives of Pennzane® X-2000, and Pennzane® X-2000 compounds containing one or more additives as a function of the thickness of the film.

Fifteen samples (Sample Nos. 17–30) that included a magnetic medium with a lubricant film formed thereon were prepared. The lubricant films were deposited on amorphous hydrogenated carbon overcoated disks using the dip procedure described in Example 2. The fifteen lubricant films were formed by dipping the magnetic medium into a solution containing the respective compositions at a specified weight percentage. Cyclohexane was used as solvent for Sample Nos. 17–30.

Sample No. 17 was a lubricant film made from a solution containing Pennzane® X-2000, Irganox® L109, and Dow® X-1P in a ratio of 90:5:5 by weight having a thickness of 10.85 Å. Sample No. 18 was a lubricant film made from a solution containing Pennzane® X-2000 and Irganox® L109 in a ratio of 95:5 by weight having a thickness of 11.95 Å. Sample No. 19 was a lubricant film made from a solution containing Pennzane® having a hydroxyl functional group represented by the following formula:

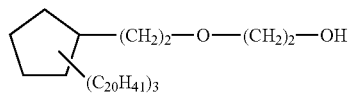

and Irganox® L109 in a ratio of 99.7:0.3 by weight having a thickness of 12.83 Å. Sample No. 20 was a lubricant film made from a solution containing Pennzane® X-1000 at 0.11 wt. % having a thickness of 14.40 Å. Pennzane® X-1000 is a dialkyl cyclopentane available from Pennzoil-Quaker State, Inc., Houston, Tex. having a molecular weight of 628. Sample No. 21 was a lubricant film made from a solution containing Pennzane® D-900 at 0.11 wt. % having a thickness of 14.17 Å. Pennzane® D-900 is a trialkyl cyclopentane available from Pennzoil-Quaker State, Inc., Houston, Tex. having an average molecular weight of 594. Sample No. 22 was a lubricant film made from a solution containing Pennzane® D-600 at 0.11 wt. % having a thickness of 13.50 Å. Sample No. 23 was a lubricant film made from a solution containing Pennzane® X-2000 at 0.055 wt. % having a thickness of 13.26 Å. Sample No. 24 was a lubricant film made from a solution containing a Pennzane® dimer amine represented by the following formula:

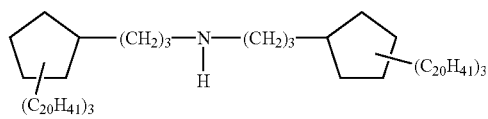

at 0.055 wt % having a thickness of 12.59 Å. Sample No. 25 was a lubricant film made from a solution containing the hydroxyl substituted Pennzane® of Sample No. 19 at 0.055 wt. % having a thickness of 12.05 Å. Sample No. 26 was a lubricant film made from a solution containing a Pennzane® dimer amine at 0.055 wt % having a thickness of 11.38 Å. Sample No. 27 was a lubricant film made from a solution containing Pennzane® having an amine functional group represented by the following formula:

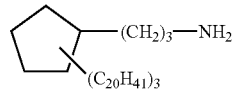

at 0.055 wt. % having a thickness of 13.03 Å. Sample No. 28 was a lubricant film made from a solution containing Pennzane® X-2000, Irganox® L109, and tricresyl phosphate in a ratio of 85:10:5 by weight having a thickness of 11.05 Å. Sample No. 29 was a lubricant film made from a solution containing Pennzane®, Irganox® L109, and tricresyl phosphate in a ratio of 90:5:5 by weight having a thickness of 12.69 Å. Sample No. 30 was a lubricant film made from a solution containing the amine substituted Pennazane® of Sample No. 27 and tricresyl phosphate in a ratio of 99.5:0.5 by weight having a thickness of 11.85 Å.

Figure 9:
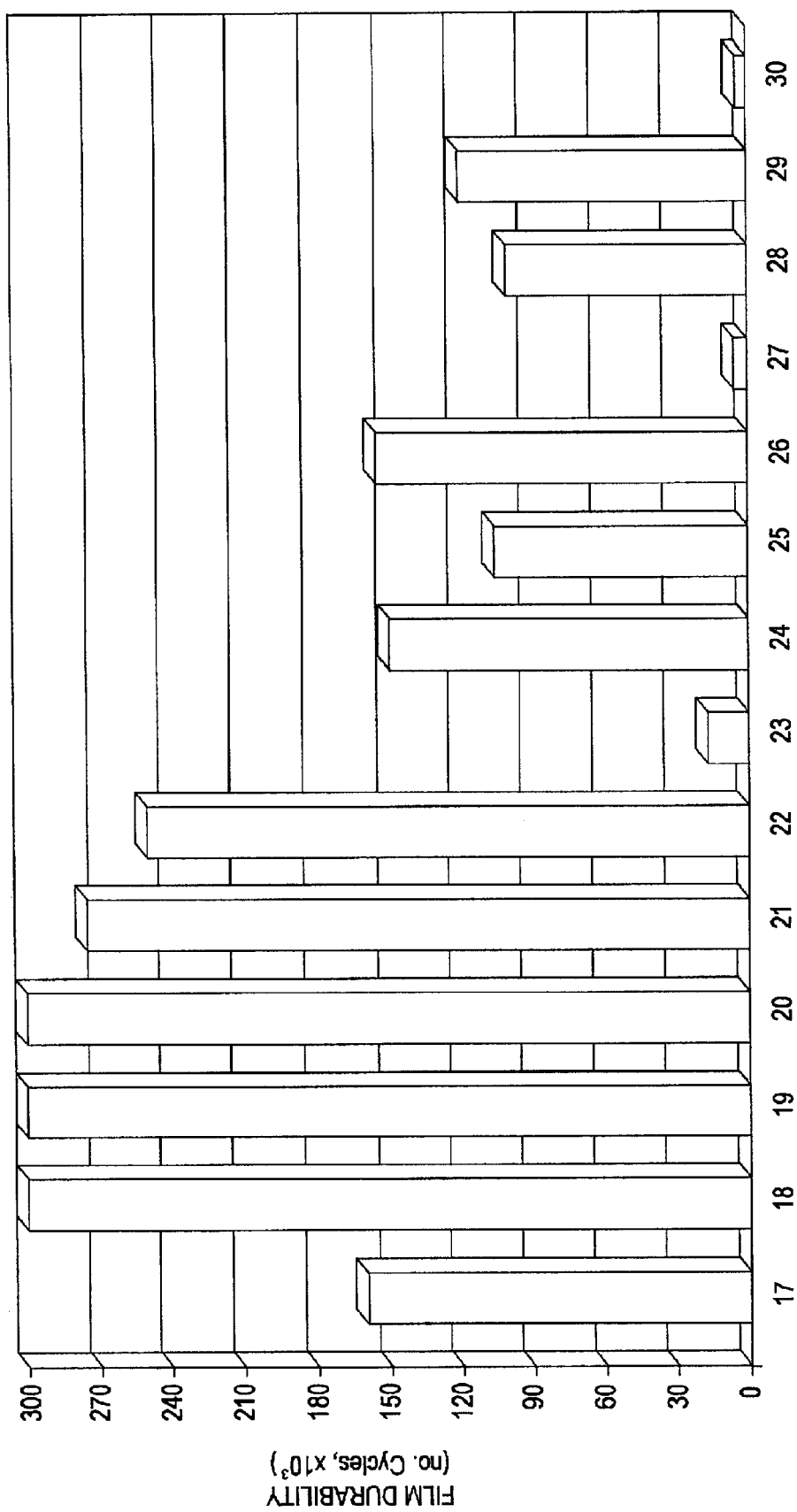
FIG. 9 is a plot which compares the film durability of various lubricants.

Sample Nos. 17–30 were tested in the HVBOIP tester using the test procedures described in Example 2 above. The number of cycles to failure was also measured, and the data are present in Table VII and FIG. 9.

TABLE VII

| Sample No. | Lubricant | Film Thickness (Å) | Number of Cycles to Failure |
|---|---|---|---|
| 17 | Pennzane ® X-2000 containing a hindered phenolic antioxidant and phosphazine | 10.85 | 160,000 |
| 18 | Pennzane ® X-2000 containing a hindered phenolic antioxidant | 11.95 | 300,000 |
| 19 | Pennzane ® having a hydroxyl functional group containing a hindered phenolic antioxidant | 12.83 | 300,000 |
| 20 | Pennzane ® X-1000 | 14.40 | 300,000 |
| 21 | Pennzane ® D-900 | 14.17 | 275,000 |
| 22 | Pennzane ® D-600 | 13.50 | 250,000 |
| 23 | Pennzane ® X-2000 | 13.26 | 17,000 |
| 24 | Pennzane ® dimer amine | 12.59 | 150,000 |
| 25 | Pennzane ® having a hydroxyl functional group | 12.05 | 105,000 |
| 26 | Pennzane ® dimer amine | 11.38 | 155,000 |
| 27 | Pennzane ® having an amine functional group | 13.03 | 5,000 |
| 28 | Pennzane ® X-2000 containing a hindered phenolic antioxidant and tricresyl phospate | 11.05 | 100,000 |
| 29 | Pennzane ® X-2000 containing a hindered phenolic antioxidant and tricresyl phospate | 12.69 | 120,000 |
| 30 | Pennzane ® having an amine functional group containing tricresyl phosphate | 11.85 | 4,500 |

It is notable that films containing Pennzane® X-2000 containing a hindered phenolic antioxidant additive and films containing low molecular weight Pennzane® compounds (i.e., films containing Pennzane® D-600, Pennazane® D-900, and Pennzane® X-1000) were among the most durable. Therefore, disk drives incorporating additives and hindered phenolic antioxidants in particular or similar lubricants should have longer lifetime and improved performance.

As demonstrated above, embodiments of the invention provide a lubricant layer for a magnetic recording medium so that the areal density of such a magnetic recording medium may be increased substantially. The suitable lubricants are less costly than some of the existing lubricants, such as PFPEs. A magnetic recording medium incorporating such a lubricant film makes it possible to manufacture higher-density computer disks, compact disks, audio tapes, and video tapes. Formation of the lubricant films according to embodiments of the invention does not require the use of environmentally-hazardous solvents, such as chlorofluorohydrocarbons. Therefore, embodiments of the invention are more environmentally-friendly than some of the existing methods. Furthermore, the lubricants used in embodiments of the invention are more resistant to chemical degradation that may occur in the data storage/retrieval process. They also have substantially higher additive solubility than PFPEs. They also have greater compatability with hydrocarbon lubricants than PFPEs. Other properties and advantages are apparent to a person of ordinary skill in the art.

While the invention has been described with a limited number of embodiments, modifications and variations therefrom exist. For example, although suitable lubricants are described with respect to hydrocarbyl-substituted cyclopentanes, cyclopentenes, and cyclopentadienes, other derivatives therefrom also may be used to form a lubricant film over a magnetic recording medium. The derivatives may include phenyl substitution, amine substitution, and so on. Furthermore, it is possible to incorporate a polymerizable unit or moiety into the above-described lubricant to render them polymerizable. Moreover, these lubricants may further be functionalized to strengthen the bonding between the lubricant layer and the underneath layer. While the invention is described with reference to a magnetic recording medium, this invention may be applied to any information storage/retrieval system, which requires a lubricant film or layer. Specifically, the invention is not limited to a contact-stop-start information storage/retrieval system.

Furthermore, although suitable additives are described for use in the lubricant layer, other additives can be used. For example, other additives such as applicability improvers, thickening agents, ultraviolet light absorbers, stabilizers, surfactants, heat stabilizers, flow improvers, release agents, dispersants, detergents, antioxidants, polymeric additives, corrosion inhibitors, rust inhibitors, oxidation inhibitors, extreme pressure agents, metal passivators, extreme pressure additives, metal deactivators, demulsifiers, metallic detergents, and combinations thereof may also be used in forming the lubricant layer. This list is meant to be an illustrative but nonlimiting list of the various additives for use in the lubricant layer. The selection of the appropriate additive could readily be determined by a person skilled in the art of lubricant formulating. Some of the above-mentioned additives can provide a multiplicity of effects. For example, a single additive may act as both a friction modifier and an antiwear agent.

The appended claims are intended to cover all modifications and variations as falling within the scope of the invention.

What is claimed is:

1. A magnetic recording medium, comprising:
a non-magnetic support;
a magnetic layer formed on the support; and
a lubricant layer over the magnetic layer, the lubricant layer including a compound selected from a hydrocarbyl-substituted cyclopentane, a hydrocarbyl-substituted cyclopentene, a hydrocarbyl-substituted cyclopentadiene, and mixtures thereof and at least one additive selected from an antioxidant, an antiwear agent, and a friction modifier, wherein the hydrocarbyl-substituted cyclopentane, hydrocarbyl-substituted cyclopentene, or hydrocarbyl-substituted cyclopentadiene are represented by the following respective formulas:

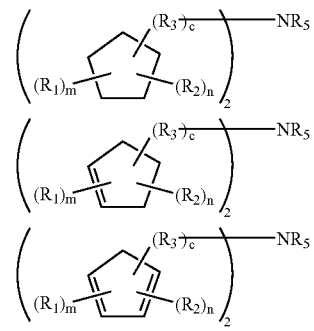

wherein c is 0, 1, 2, 3, 4, 5, 6, 7, 8, 9, or 10; m and n are zero or a positive integer; $R_1$, $R_2$, and $R_3$ are individually a hydrocarbyl group; and $R_5$ is hydrogen or hydrocarbyl.

2. A magnetic recording medium, comprising:
a non-magnetic support;
a magnetic layer formed on the support; and
a lubricant layer over the magnetic layer, the lubricant layer including a compound selected from a hydrocarbyl-substituted cyclopentane, a hydrocarbyl-substituted cyclopentene, a hydrocarbyl-substituted cyclopentadiene, and mixtures thereof and at least one additive selected from an antioxidant, an antiwear agent, and a friction modifier,
wherein the hydrocarbyl-substituted cyclopentane, hydrocarbyl-substituted cyclopentene, or hydrocarbyl-substituted cyclopentadiene are represented by the following respective formulas:

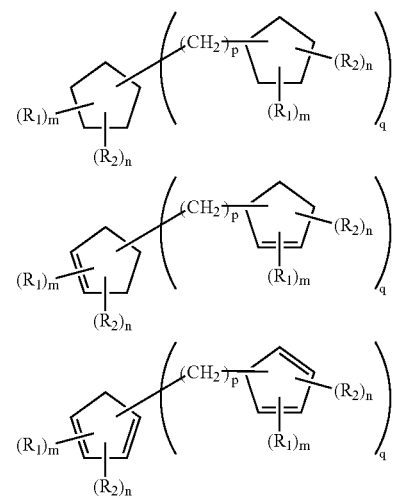

wherein p is 1, 2, 3, . . . , or 10; q is 1, 2, 3, . . . , or 10; m and n are zero or a positive integer; and $R_1$ and $R_2$ are individually a hydrocarbyl group.

3. A magnetic recording medium, comprising:
a non-magnetic support;
a magnetic layer formed on the support; and
a lubricant layer over the magnetic layer, the lubricant layer including a compound selected from a hydrocarbyl-substituted cyclopentane, a hydrocarbyl-substituted cyclopentene, a hydrocarbyl-substituted cyclopentadiene, and mixtures thereof and at least one additive selected from an antioxidant, an antiwear agent, and a friction modifier, wherein the hydrocarbyl-substituted cyclopentane, hydrocarbyl-substituted cyclopentene, or hydrocarbyl-substituted pentadiene are represented by the following respective formulas:

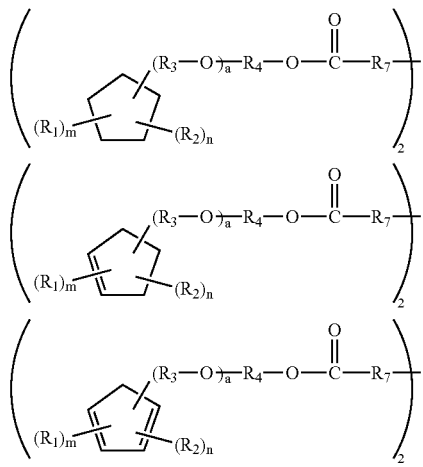

wherein a is 0, 1, 2, 3, 4, 5, 6, 7, 8, 9, or 10; m and n are zero or a positive integer; $R_1$, $R_2$, $R_3$, and $R_4$ are individually a hydrocarbyl group; and $R_7$ is a hydrocarbyl group from $C_1$ to $C_{20}$.

4. A magnetic recording medium of, comprising:

a non-magnetic support;

a magnetic layer formed on the support; and a lubricant layer over the magnetic layer, the lubricant layer including a compound selected from a hydrocarbyl-substituted cyclopentane, a hydrocarbyl-substituted cyclopentene, a hydrocarbyl-substituted cyclopentadiene, and mixtures thereof and at least one additive selected from an antioxidant, an antiwear agent, and a friction modifier, wherein the hydrocarbyl-substituted cyclopentane, hydrocarbyl-substituted cyclopentene, or hydrocarbyl-substituted pentadiene are represented by the following respective formulas:

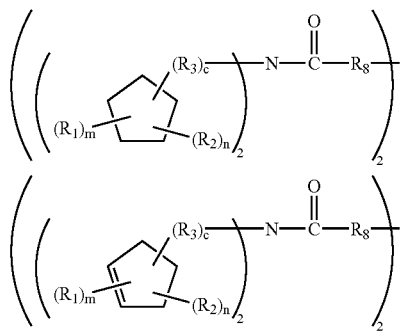

-continued

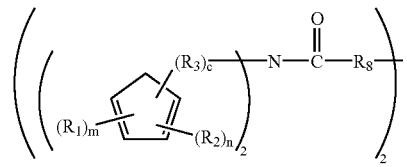

wherein c is 0, 1, 2, 3, 4, 5, 6, 7, 8, 9, or 10; m and n are zero or a positive integer; $R_1$, $R_2$, and $R_3$ are individually a hydrocarbyl group; and $R_8$ is a hydrocarbyl group from $C_1$ to $C_{20}$.

5. A magnetic recording medium comprising:

a non-magnetic support;

a magnetic layer formed on the support; and a lubricant layer over the magnetic layer, the lubricant layer including a compound selected from a hydrocarbyl-substituted cyclopentane, a hydrocarbyl-substituted cyclopentene, a hydrocarbyl-substituted cyclopentadiene, and mixtures thereof and at least one additive selected from an antioxidant, an antiwear agent, and a friction modifier, wherein the hydrocarbyl-substituted cyclopentane, hydrocarbyl-substituted cyclopentene, or hydrocarbyl-substituted pentadiene are represented by the following respective formulas:

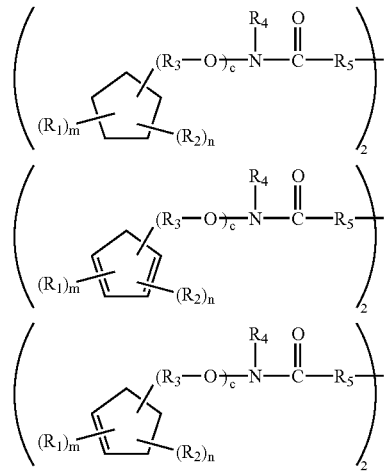

wherein c is 0, 1, 2, 3, 4, 5, 6, 7, 8, 9, or 10; m and n are zero or a positive integer; $R_1$, $R_2$, and $R_3$ are individually a hydrocarbyl group; $R_4$ is a hydrocarbyl group or hydrogen; and $R_5$ is a hydrocarbyl group from $C_1$ to $C_{20}$.

6. A magnetic recording medium, comprising:

a non-magnetic support;

a magnetic layer formed on the support;

a lubricant layer over the magnetic layer, the lubricant layer including a compound selected from a hydrocarbyl-substituted cyclopentane, a hydrocarbyl-substituted cyclopentene, a hydrocarbyl-substituted cyclopentadiene, and mixtures thereof and at least one additive selected from an antioxidant, an antiwear agent, and a friction modifier, a protective layer between the magnetic layer and the lubricant layer, wherein the hydrocarbyl-substituted cyclopentane, hydrocarbyl-substituted cyclopentene, or hydrocarbyl-substituted cyclopentadiene are represented by the following respective formulas:

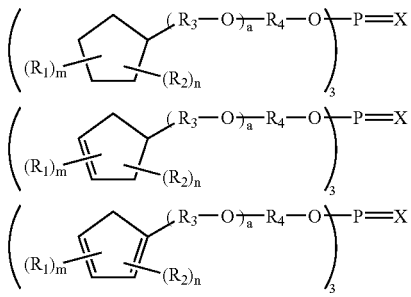

wherein a is 0, 1, 2, 3, 4, 5, 6, 7, 8, 9, or 10; m and n are zero or a positive integer; $R_1$, $R_2$, $R_3$, and $R_4$ are individually a hydrocarbyl group; and X is either oxygen.

7. The A magnetic recording medium, comprising:
a non-magnetic support;
a magnetic layer formed on the support;
a lubricant layer over the magnetic layer, the lubricant layer including a compound selected from a hydrocarbyl-substituted cyclopentane, a hydrocarbyl-substituted cyclopentene, a hydrocarbyl-substituted cyclopentadiene, and mixtures thereof and at least one additive selected from an antioxidant, an antiwear agent, and a friction modifier, and
a protective layer between the magnetic layer and the lubricant layer,
wherein the hydrocarbyl-substituted cyclopentane, hydrocarbyl-substituted cyclopentene, or hydrocarbyl-substituted cyclopentadiene are represented by the following respective formulas:

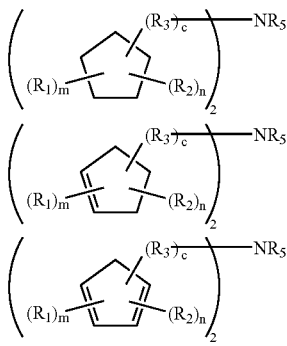

wherein c is 0, 1, 2, 3, 4, 5, 6, 7, 8, 9, or 10; m and n are zero or a positive integer; $R_1$, $R_2$, and $R_3$ are individually a hydrocarbyl group; and $R_5$ is hydrogen or hydrocarbyl.

8. A magnetic recording medium, comprising:
a non-magnetic support;
a magnetic layer formed on the support;
a lubricant layer over the magnetic layer, the lubricant layer including a compound selected from a hydrocarbyl-substituted cyclopentane, a hydrocarbyl-substituted cyclopentene, a hydrocarbyl-substituted cyclopentadiene, and mixtures thereof and at least one additive selected from an antioxidant, an antiwear agent, and a friction modifier, and
a protective layer between the magnetic layer and the lubricant layer,
wherein the hydrocarbyl-substituted cyclopentane, hydrocarbyl-substituted cyclopentene, or hydrocarbyl-substituted cyclopentadiene are represented by the following respective formulas:

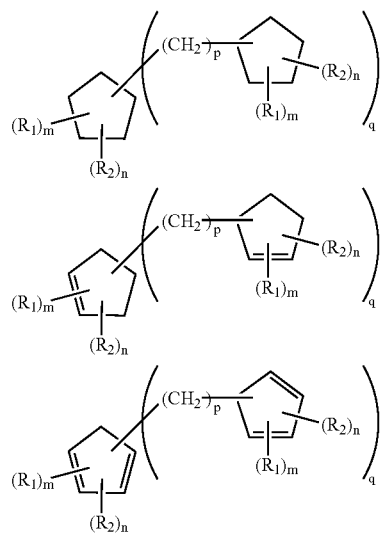

wherein p is 1, 2, 3, . . . , or 10; q is 1, 2, 3, . . . , or 10; m and n are zero or a positive integer; and $R_1$ and $R_2$ are individually a hydrocarbyl group.

9. The A magnetic recording medium, comprising:

a non-magnetic support;

a magnetic layer formed on the support;

a lubricant layer over the magnetic layer, the lubricant layer including a compound selected from a hydrocarbyl-substituted cyclopentane, a hydrocarbyl-substituted cyclopentene, a hydrocarbyl-substituted cyclopentadiene, and mixtures thereof and at least one additive selected from an antioxidant, an antiwear agent, and a friction modifier, and a protective layer between the magnetic layer and the lubricant layer, wherein the hydrocarbyl-substituted cyclopentane, hydrocarbyl-substituted cyclopentene, or hydrocarbyl-substituted pentadiene are represented by the following respective formulas:

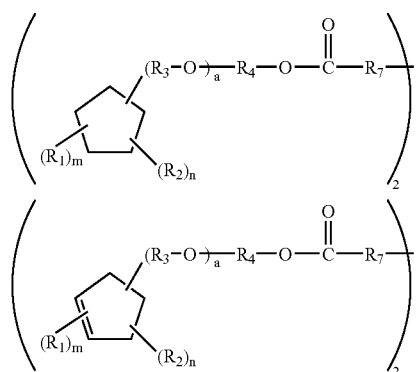

-continued

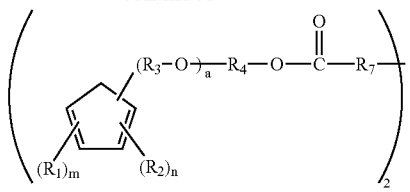

wherein a is 0, 1, 2, 3, 4, 5, 6, 7, 8, 9, or 10; m and n are zero or a positive integer; $R_1$, $R_2$, $R_3$, and $R_4$ are individually a hydrocarbyl group; and $R_7$ is a hydrocarbyl group from $C_1$ to $C_{20}$.

10. A magnetic recording medium, comprising:
a non-magnetic support;
a magnetic layer formed on the support;
a lubricant layer over the magnetic layer, the lubricant layer including a compound selected from a hydrocarbyl-substituted cyclopentane, a hydrocarbyl-substituted cyclopentene, a hydrocarbyl-substituted cyclopentadiene, and mixtures thereof and at least one additive selected from an antioxidant, an antiwear agent, and a friction modifier, and
a protective layer between the magnetic layer and the lubricant layer,
wherein the hydrocarbyl-substituted cyclopentane, hydrocarbyl-substituted cyclopentene, or hydrocarbyl-substituted pentadiene are represented by the following respective formulas:

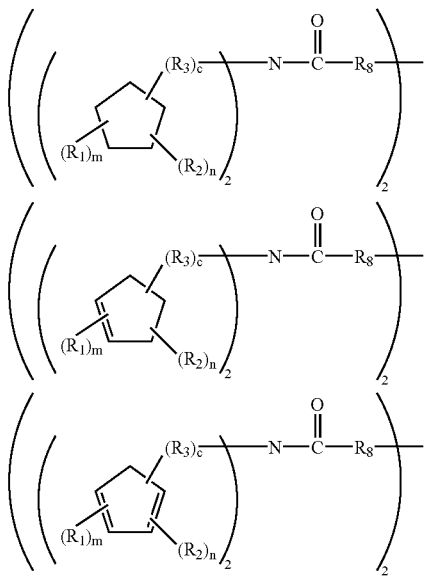

wherein c is 0, 1, 2, 3, 4, 5, 6, 7, 8, 9, or 10; m and n are zero or a positive integer; $R_1$, $R_2$, and $R_3$ are individually a hydrocarbyl group; and $R_8$ is a hydrocarbyl group from $C_1$ to $C_{20}$.

11. A magnetic recording medium, comprising:

a non-magnetic support;

a magnetic layer formed on the support;

a lubricant layer over the magnetic layer, the lubricant layer including a compound selected from a hydrocarbyl-substituted cyclopentane, a hydrocarbyl-substituted cyclopentene, a hydrocarbyl-substituted cyclopentadiene, and mixtures thereof and at least one additive selected from an antioxidant, an antiwear agent, and a friction modifier, and a protective layer between the magnetic layer and the lubricant layer, wherein the hydrocarbyl-substituted cyclopentane, hydrocarbyl-substituted cyclopentene, or hydrocarbyl-substituted pentadiene are represented by the following respective formulas:

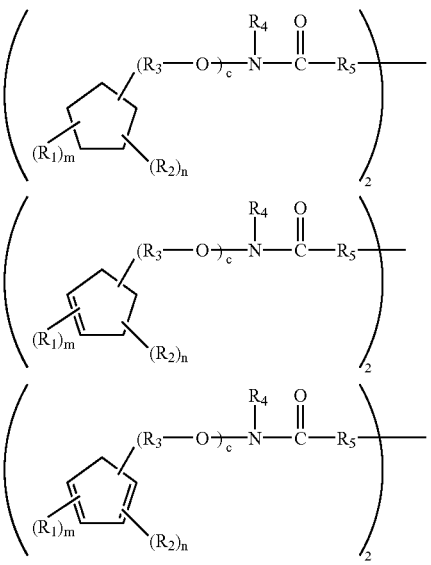

wherein c is 0, 1, 2, 3, 4, 5, 6, 7, 8, 9, or 10; m and n are zero or a positive integer; $R_1$, $R_2$, and $R_3$ are individually a hydrocarbyl group; $R_4$ is a hydrocarbyl group or hydrogen; $R_5$ is a hydrocarbyl group from $C_1$ to $C_{20}$.

* * * * *